US008163544B2

(12) United States Patent
Hammond et al.

(10) Patent No.: US 8,163,544 B2
(45) Date of Patent: Apr. 24, 2012

(54) METHODS AND COMPOSITIONS FOR INCREASING TISSUE TROPISM OF RECOMBINANT ADENOVIRAL VECTORS

(75) Inventors: Jeffrey Hammond, Aldershot (GB); Michael A. Johnson, Pirbright (GB)

(73) Assignee: Commonwealth Scientific and Industrial Research Organisation, Campbell, ACT (AU)

( * ) Notice: Subject to any disclaimer, the term of this patent is extended or adjusted under 35 U.S.C. 154(b) by 0 days.

(21) Appl. No.: 12/373,772

(22) PCT Filed: Jul. 27, 2007

(86) PCT No.: PCT/IB2007/002710
§ 371 (c)(1), (2), (4) Date: Dec. 2, 2009

(87) PCT Pub. No.: WO2008/012682
PCT Pub. Date: Jan. 31, 2008

(65) Prior Publication Data

US 2010/0104600 A1 Apr. 29, 2010

Related U.S. Application Data

(60) Provisional application No. 60/833,985, filed on Jul. 28, 2006.

(51) Int. Cl.
*C12N 15/861* (2006.01)
*A61K 39/12* (2006.01)
*A01N 63/00* (2006.01)

(52) U.S. Cl. .................. 435/320.1; 424/199.1; 424/93.6

(58) Field of Classification Search ........................ None
See application file for complete search history.

(56) References Cited

U.S. PATENT DOCUMENTS

| | | | | |
|---|---|---|---|---|
| 6,492,343 | B1 | 12/2002 | Reddy et al. | |
| 7,232,899 | B2 | 6/2007 | Von Seggern et al. | |
| 2002/0034519 | A1 | 3/2002 | Tikoo et al. | |
| 2003/0219899 | A1 | 11/2003 | Korokhov | |
| 2010/0104600 | A1* | 4/2010 | Hammond et al. | 424/233.1 |

FOREIGN PATENT DOCUMENTS

| | | |
|---|---|---|
| WO | WO 99/08706 | 2/1999 |
| WO | WO 99/55365 | 11/1999 |
| WO | WO 02/24933 | 3/2002 |

OTHER PUBLICATIONS

Amalfitano et al., Gene Ther., 4(3):258-263 (1997).
Amalfitano et al., Proc. Natl. Acad. Sci. USA, 93(25):14314 (1996).
Chiu et al., J. Virol., 75(11):5375-5380 (2001).
Dmitriev et al., J. Virol., 72(12):9706-9713 (1998).
Dolph et al., J. Virol., 62(6):2059-2066 (1988).
Dolph et al., J. Virol., 64(6):2669-2677 (1990).
Einfeld et al., J. Virol., 73(11):9130-9136 (1999).
Gall et al., J. Virol., 70(4):2116-2123 (1996).
Jakubczak et al., J. Virol., 75(6):2972-2981 (2001).
Krashnykh et al., J. Virol., 70(10):6839-6846 (1996).
Magnusson et al., J. Virol., 75(16):7280-7289 (2001).
Melkonyan et al., Nucl. Acids Res., 24(21):4356-4357 (1996).
Morrison et al., J. Gen. Virol., 78(Pt 4):873-878 (1997).
Reddy et al., J. Virol., 72(2):1394-1402 (1998).
Shayakhmetov et al., J. Virol., 74(6):2567-2583 (2000).
Sprengel et al., J. Virol., 68(1):379-389 (1994).
Stevenson et al., J. Virol., 71(6):4782-4790 (1997).
Von Seggern et al., J. Gen. Virol., 79(Pt 6):1461-1468 (1998).
Von Seggern et al., J. Virol., 73(2):1601-1608 (1999).
Von seggem et al., J. Virol., 74(1):354-362 (2000).
Wickham et al., J. Virol., 71(11):8221-8229 (1997).
Wirtz et al., Gut, 44(6):800-807 (1999).
Zhang et al., J. Virol., 68(11):7040-7050 (1994).
Zoller et al., Nuc. Acids Res., 10(20):6487-6500 (1982).
International Preliminary Report on Patentability corresponding to International Application International Application No. PCT/IB2007/002710, dated Feb. 3, 2009.
Takayama et al., "A mosaic adenovirus possessing serotype Ad5 and serotype Ad3 knobs exhibits expanded tropism." Virology 309, 2002, pp. 282-293.
Brennan et al., Roux's Arch. Dev. Biol., 199:89-96 (1990).
Chow et al., Cell, 12(1):1-8 (1977).
Chroboczek et al., Curr. Top Microbiol. Immunol., 199(Pt 1):163-200 (1995).
Davison et al., J. Mol. Biol., 234(4):1308-1316 (1993).
Derbyshire et al., J. Comp. Pathol., 85(3):437-443 (1975).
Douglas et al., Nat. Biotechnol., 17(5):470-475 (1999).
Hammond et al., Arch. Virol., 146(9):1787-1793 (2001).
Hammond et al., Vaccine, 18(11-12):1040-1050 (2000).
Hammond et al., Virus Res., 97(2):151-157 (2003).
Hirahara et al., Nippon Juigaku Zasshi, 52(2):407-409 (1990).
Hirt, J. Mol. Biol., 26(2):365-369 (1967).
Kadoi et al., New Microbiol., 20(3):215-220 (1997).
Kadoi, New Microbiol., 20(1):89-91 (1997).
Kleiboeker, Virus Res., 31(1):17-25 (1994).
Kleiboeker, Virus Res., 36(2-3):259-268 (1995).
Kleiboeker, Virus Res., 39(2-3):299-309 (1995).
Kunkel et al., Methods Enzymol., 154:367-382 (1987).
Li et al., Virus Res., 104(2):181-190 (2004).
McCoy et al., Arch. Virol., 141(7):1367-1375 (1996).
McCoy et al., DNA Seq., 6(4):251-254 (1996).
Reddy et al., Arch. Virol., 140(1):195-200 (1995).
Reddy et al., Intervirology, 36(3):161-168 (1993).
Reddy et al., Virology, 212(1):237-239 (1995).
Reddy et al., Virology, 251(2):414-426 (1998).
Reddy et al., Virus Genes, 15(1):87-90 (1997).
Reddy et al., Virus Res., 36(1):97-106 (1995).
Reddy et al., Virus Res., 43(2):99-109 (1996).
Shannon et al., Vet. Microbiol., 34(3):233-248 (1993).
Sheay et al., Biotechniques, 15(5):856-862 (1993).
Shinagawa et al., Microbiol. Immunol., 27(9):817-822 (1983).
Shiraishi et al., J. Surg. Res., 76(2):105-110 (1998).
Terpstra et al., Vet. Microbiol., 9(2):113-120 (1984).

(Continued)

*Primary Examiner* — Michael Burkhart
(74) *Attorney, Agent, or Firm* — McAndrews, Held & Malloy Ltd.

(57) ABSTRACT

Methods are provide to allow for the preparation of adenoviral vectors with altered tropism. Compositions comprising such vectors and methods of use thereof also are provided.

13 Claims, 10 Drawing Sheets

OTHER PUBLICATIONS

Tuboly et al., Res. Vet. Sci., 54(3):345-350 (1993).
Vrati et al., Virology, 209(2):400-408 (1995).
Wang et al., Gene Ther., 2:775-783 (1995).
Watkins et al., Gene Ther., 4:1004-1012 (1997).
Zheng et al., Virus Res., 31:163-186 (1994).
Schoggins et al., J. Virol., 77(2):1039-1048 (2003).
Hammond et al., Vet. J., 169(1):17-27 (2005).
Supplementary European Search Report in EP 07804942.6, dated May 26, 2010.
Office Action in CN 200780026689.3, dated Sep. 7, 2011.

* cited by examiner

PAdV3 fibre

MGPKKQKRELPEDFDPVYPYDVPQLQINPPFVSGDGFNQSVDGVLSLHIA
PPLVFDNTRALTLAFGGGLQLSGKQLVVATEGSGLTTNPDGKLVLKVKSP
ITLTAEGISLSLGPGLSNSETGLSLQVTAPLQFQGNALTLPLAAGLQNTD
GGMGVKLGSGLTTDNSQAVTVQVGNGLQLNGEGQLTVPATAPLVSGSAGI
SFNYSSNDFVLDNDSLSLRPKAISVTPPLQSTEDTISLNYSNDFSVDNGA
LTLAPTFKPYTLWTGASPTANVILTNTTTPNGTFFLCLTRVGGLVLGSFA
LKSSIDLTSMTKKVNFIFDGAGRLQSDSTYKGRFGFRSNDSVIEPTAAGL
SPAWLMPSTFIYPRNTSGSSLTSFVYINQTYVHVDIKVNTLSTNGYSLEF
NFQNMSFSAPFSTSYGTFCYVPRRTTHRPRHGPFSLRERRHLFQLLQQ
CGGDFDPVYPYD

PAdV4 fibre

MKRSVPSDFNPVYPYDYQPISLMPAFYDNYGFHEGPSGVLSLNIANPLGY
TPRKKLCLKLGEGLALDSDGHLRVQIPDMQAQPPLLYQGHRLSLLFDADA
GFHLTEDGALSLTKTLVYPTLWTGPAPEANVTFSGENSPSGILRLCLSRT
GGTVIGTLSVQGSLTNPSTGQTLGMNLYFDADGNVLSESNLVRGSWGMKD
QDTLVTPIANGQYLMPNLTAYPRLIQTLTSSYIYTQAHLDHNNSVVDIKI
GLNTDLRPTAAYGLSFTMTFTNSPPTSFGTDLVQFGYLGQDSSPSFLREL
PLASEAGYFGKLAAASEEMPAPPEAQTQDQAAEEPPAPAEAEAPAPAEAE
AEAEPPRKPPRGDLAALYNRVHSDTRAEDTPTSPELVTTLPDPFVLPLPD
GVPTGASIVLEGTLTPSAVFFTLDLVTGPASLALHFNVRLPLEGEKHIVC
NSREGSSNWGEEVRPQEFPFEREKPFVLVIVIQSDTYQITVNGKPLVDFP
QRLQGITRASLSGDLVFTRLTMYPPGDPRPTTLLPPPAAPLDVIPDAYVL
NLPTGLTPRTLLTVTGTPTPLAEFFIVNLVYDLHYDSKNVALHFNVGFTS
DSKGHIACNARMNGTWGSEITVSDFPFQRGKPFTLQILTREADFQVLVDK
QPLTQFQYRLKELDQIKYVHMFGHVVQTHLEHQVPDTPVFSTAGVSKVYP
QIL

Figure 4

SEQUENCE LISTING

<160> NUMBER OF SEQ ID NOS: 14

<210> SEQ ID NO 1
<211> LENGTH: 2162
<212> TYPE: DNA
<213> ORGANISM: Porcine adenovirus 4

<400> SEQUENCE: 1
aacccacctg gaacaccaag tgccagatgc tccagttttt tctaccgcgg gagtttcgaa 60
agtttaccct cagatactgt agtcagacac aaagatgtaa ctgccwgcat gagaaagttt 120
attggcaata aagctactgg aaacgatgcg tgtggtgatc tttccccctc ccccaaattt 180
cattttgtaa cataccctat gggaaggccc cggcccacag tcagccacag tctcaagttg 240
ctccagctca ggtgaggtaa tgctgatgaa cccaggcgat atcagtctcg catccaaggt 300
gtgatccaaa ctctgtgaaa atcatactcc gcttgtaaac tttcgccaag gcaccggggt 360
tccatacacc atcaatcttc gcagacgtcg ccgccgtgcg ccgtcccgaa aagccgggta 420
gaacactctc ggtcgaggtc ccccaactct cagcaaccta aaagcctcct gaagcaactc 480
cctgctctga accgcacact gcctcacatc acgttcatgc agagacatac atccagtaca 540
caagcgtata aagtagtaat tagttgcagt acagagaaat ttcacagacg ggcctgacag 600
ttgctgcttc aaaagccaaa agtcattccc ctgtctgcag caaaacacca caaagtgcag 660
ccccgccacc atataggagc ccctgcaaga gatagcttta ggtaagtcaa cacacaccct 720
cttctgcata ccagatgaag ctgcggttaa agaaacagcc cctgggatca cagacgtagc 780
caaaggtctt caccaccaca ctcctagccc tacattgcaa gagagtgrgg gctgtcacag 840
ktgrmcaatg tatagaaagc acctctcgac catacaagta atttccccsa awacagattg 900
tttaactcca aggscccggg ggccagaccc atcccagttc tacggagaca ttgcaaagtg 960
gagccagaag caaccaaatc ccaaggcacc ggaagatcta agtaagctgt gaaacatgct 1020
gcaggtggag tggtgcttac cgctccaact agatgcttag agtcacatgg ttcaacagaa 1080
gtcattgtcc tggaagagga agagggaaag cattaaagca ccgaaacagc tcaatggggg 1140
ggctggtgtg gtacacagcc accatacggg aaccaagaaa agtcaacagg ccagaggcca 1200
aatcctgctg ggactccgga gttgcaaaca gccgagagcc cgccgtgact gtgatagtgt 1260
gcctgccttg aggtaaatca agcatgcagc aacaatgcag aaaagactca gagcgagtac 1320
cagggcgagt ttccaaatca aagcgaatca gcaagtaatc ataaaccaag gatctgatca 1380
catccagcca aagswckwcm cgaaggcaaa gtaggatccc ctggcacatc cgtgatgtac 1440
aggtgccagg accaagcgct gtacacgaaa gtgccggacg ccatcttgcg tacagatcac 1500
tgacccgtgg agccgaaacc gccggcaccc ctgtcggtag gctgcaggtc gtccaccagc 1560
tggcacacgg gtctctcaaa tttcaggaaa accagctgcg cgatccggtc cccgggagcg 1620
ataaacacag gcagaggccc actgttcgcc aacagcactt tcactcgcct gtaagtccgg 1680

-continued

```
gtcaattgtt cccgcacaga cgtacacgcc gcgcaacgac aactcgatcg tgaaaaaatc   1740

tgcccgtagg gcccaggcgg aggacttatg gcgatcccag aacggatgat agttcggtcc   1800

cccggttcca tgatacgagc ctccggcgag caaaacgtct atccccgtg aagccgccgt    1860

accgaaaaca gccggccccc cccgtcccgc taacttcccc tttaagatcc ggagtggtcc   1920

tgacggctca gagggaaaaa ccgcgaaaaa attccgcgaa ctccgcaaaa acccgaacgg   1980

agtaccgccc ccgggaatcc gtgaactgac attggccgac ttttatggcg cccggcatgt   2040

cgatagtgac aatacgggaa gggaaccaat tcacgcattc tgggcagtgt gggagaaagc   2100

ggacttacac aatgtgtctt cgcaccacgg gaaaagatta ctcgatacct cataaggtga   2160

tg                                                                  2162
```

<210> SEQ ID NO 2
<211> LENGTH: 1732
<212> TYPE: DNA
<213> ORGANISM: Porcine Adenovirus 1

<400> SEQUENCE: 2

```
tataaaccag ttccaccatg ggaccgaaga agcagaagcg cgagctcccc gaggacttcg     60

atccagtcta cccctatgac gccccgcagc tgcagatcaa tccacccttc gtcagcgggg    120

acggattcca ccaatccgtg gacggggtgc tgtccctgca catcgcaccg cccctcgtct    180

ttgacaacac cagggccctc accctggcct tcggggatgg tctacagctc tttaacaaca    240

agctcatcgt tgccactgag ggatctgggc tggtcatcac cacggatggc aagctggtcc    300

tccaggtcac ctccccccctc accctagcac ccgatggcat ctcccctgtc cctgggcccc    360

cggtctctct agctcaagat gacaagactc agccstgcaa ggtcacatct cccctgcagc    420

tccaaaagca actccctcgc cctttccctc ggcagcggtc tccaaaacac cgagggtggc    480

cgtagcttgt caagctgggg gctggtctca ccacggacaa cagtcagtca gtgacagtca    540

aggtgggaga cggtcttaag ctgaacgaag gagggctgct caccgtcccc gtaacagcac    600

cacttgtgtc cggcgcaccc ggactatcac tttaactact cctccactga tttcgaactt    660

gataacggca gcctccgtct gcgtcctaag ccgatctccg tcacggcgcc actgcaatct    720

accgctgaca ccatctccct gaagtattct gacactgact tctctttgga ggataacacc    780

accctcactt taacacctaa attaaaaccg tacacactgt ggaccggtaa ttcagataca    840

gctaatgtga tcctcaatca cagctccacc cccaatggta cattatttct atgtctgaca    900

cgtgtgggtg grtagtttta gcactttgcc ctgaagacat catccctaca tttagtgata    960

tgacaaacag ctatcttatt tttgatactt tgtcgactca gactctcact tataggagtt   1020

tgattagatc aacacgacgt cattagccca cagtccacag gactcagtcc agcctggtta   1080

atgccaagca cctttattta ccctaactca tcgggctcaa ctttgacatc attcgtaaga   1140

attaaagcaa caaatgttca tgtggatatc agagtcaaca gcctctccac taacggtttt   1200

agtcttcagt ttgaatttga aaacatgatc atctccagtg ccttctccac ctcctacggg   1260

accttctgct acgtgcccca gagtgcctag agaaccctgg ccgtcagccg gcctccccct   1320

tcccatacca cccggtagac cacccgctcc atgtttctgt atgtgttctc ctcccgccgc   1380

ttgtgcagca ccacctcccg ctgctcgagc tgaggatccg tgatggacac aaagccagga   1440

agacacatcc tcagctccgt gggggcgtcc aacaactgtt tgtgcaagga aaatatgaaa   1500

caataaagac tcagagaaaa acaagttcat atgatttttt cttttattga ttgggggatt   1560

tgattcaggt ggggtgtaca tatcacaaaa aaatcacatc agcagctaca ccctggaaac   1620
```

```
attcagacag gggtaaggac agcgccctca gcttctggaa caaacattag aaatatttaa   1680

ctcgtcttgg agctaacact ctttttccca gaacacataa acatcctgta ga           1732


<210> SEQ ID NO 3
<211> LENGTH: 968
<212> TYPE: DNA
<213> ORGANISM: Porcine Adenovirus 2
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (229)..(229)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (382)..(382)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t

<400> SEQUENCE: 3

agtggggttc aaaaaagtta cataancgcg cttctcgtgc agagagagcc gggnanngcg     60

cctcttcagc agtgggtcgt gggccgtgag agggggctga tgggaagatg gccggtgact    120

cctctcgccc cgctttcggc ttctcctcgt ctcgctctcc ttgtctctct ctgtgtcagc    180

gcagaaacta gtgtgagcga acaacgcgag ggggccggtg atatacccnc agctgatgtg    240

gccacagctg ctatcggnta atcactaccc catcgtacga tcgnaattcc cccgcctcct    300

cgttncgatt aacccaccca gaagtctcgg gaattcccgc cagccgggct ccgacccgcg    360

acgtgcggac tttgaccccg cncctcggac attgaccggt cccacgccac gtcactttcc    420

cactcgacgt cccgttcccg cgctncgtca cacccctctc catgaatctg ctgcaaccgc    480

ctcgaaccct ctcttccaat caactcgcca ttaaaggggc aataaaagtg tagggtatat    540

ggattgatga tggcccaggt gaccaggtcc gagcgcttga tcgattccgt gggaagtgga    600

tgtcagctaa gctcctaatg acaaccgcca accacggctg cagaagctct tccctctaga    660

gacgcgagct agcatagaca tactccatct atacactcgc cgtagacaat gtcatacgca    720

aatgggagga ctaaggacat cccggatcca ccacctggga tgtactccat ccatcgggac    780

acttaaacag caataagaaa gacgcaattg ttgacgcaga aatttggcta gagaggcggg    840

caggactcat gagcctagag accacccaat tgggaaagtg acctcccctc cccccgtgga    900

aaacgtggta tcaaacgaga tcgacaatgc aattcggtca ctttaggggt acgaggatat    960
```

atcacgga 968

<210> SEQ ID NO 4
<211> LENGTH: 1174
<212> TYPE: DNA
<213> ORGANISM: Porcine Adenovirus 2

<400> SEQUENCE: 4
aaaaaaggca ggagcgatga ttgatagctc gaggaatagc tcagtcacca catcccttcc 60
ctgcaccact tataagggta tatataggca gagacacaga caatcagtca tcatcacatg 120
ctgtttattg aggttaatga ttaatcgcgg gggcgcttca tagacaggtc caaaggttgt 180
tcgctgcatg agtcatagca gtacttcctc ttgcgtcctg gcaggtctcc aagtcccggg 240
gaacccgacc tgtgaggtgc tggagaaaca gcttctaaaa agacaaaaaa tgggaaatag 300
cacatgagat ttcttacaag cactttttcc ttttttcca cataatccca caaatgtcca 360
aaaacactca ccatagacag caaaggcatg catcctcatg tagcacagac tgcacttcag 420
attggggtcc ttggagtgaa agcgatggta atcacaagag cggcagttca caccaggtac 480
ctcggggcag tccaacacaa acggagggtg gcgcaagtgg gtcctcaaac accacatcag 540
ccagttcaga cagcacctcc gcagccaccg cgctgatatc ctcctcatta ctgtcccccct 600 cttctggggg gtccatctca aagacccccct gagagccacc tgagtcacca gcggcactcc 660
caccactgtc ctcagctaca cccccctcag tcacaatcac ctccacctcg tccacactgt 720
ccagccactc gtccggcagt ccatcgacca gactctccca gcacggctca cagaagccct 780
catcccccgg agaggggtcg cgcagatcca ccgggtccca ttccagcacc ggcaccacct 840
cggggtttcc gtcccagtcc aggtgaagtc tgttcgccat gtcgagggtc tgttccgctg 900
agagaaaact ctactccctt cggactcaag agtagtgact ctcgggcgct gcgcggacta 960
tatacactga ggagaaaaaa tacacccaca cacgtcatct cgggcgggcg ccgcgacctc 1020
tcagcgcgaa ggaaaccccg gctcaggtga atggtgtccc gtcgtcagtg gggatacgag 1080
cggcgacggt gtgtggaaat gccacaccgg agggcgaggg tcagtccaaa agcaaaaatt 1140
cccgctaact tccacttgtt ggaaatatct ctgc 1174

<210> SEQ ID NO 5
<211> LENGTH: 1176
<212> TYPE: DNA
<213> ORGANISM: Porcine Adenovirus 2

<400> SEQUENCE: 5
gcagagatat ttccaacaag tggaagttag cgggaatttt tgcttttgga ctgaccctcg 60
ccctccggtg tggcatttcc acacaccgtc gccgctcgta tccccactga cgacgggaca 120
ccattcacct gagccggggt ttccttcgcg ctgagaggtc gcggcgcccg cccgagatga 180
cgtgtgtggg tgtatttttt ctcctcagtg tatatagtcc gcgcagcgcc cgagagtcac 240
tactcttgag tccgaaggga gtagagtttt ctctcagcgg aacagaccct cgacatggcg 300
aacagacttc acctggactg ggacggaaac cccgaggtgg tgccggtgct ggaatgggac 360
ccggtggatc tgcgcgaccc ctctccgggg gatgagggct tctgtgagcc gtgctgggag 420
agtctggtcg atggactgcc ggacgagtgg ctggacagtg tggacgaggt ggaggtgatt 480
gtgactgagg ggggtgtagc tgaggacagt ggtgggagtg ccgctggtga ctcaggtggc 540
tctcaggggg tctttgagat ggacccccca gaagaggggg acagtaatga ggaggatatc 600
agcgcggtgg ctgcggaggt gctgtctgaa ctggctgatg tggtgtttga ggacccactt 660

-continued

```
gcgccaccct ctccgtttgt gttggactgc cccgaggtac ctggtgtgaa ctgccgctct    720

tgtgattacc atcgctttca ctccaaggac cccaatctga agtgcagtct gtgctacatg    780

aggatgcatg cctttgctgt ctatggtgag tgtttttgga catttgtggg attatgtgga    840

aaaaaaggaa aaagtgcttg taagaaatct catgtgctat ttcccatttt ttgtcttttt    900

agaagctgtt tctccagcac ctcacaggtc gggttccccg ggacttggag acctgccagg    960

acgcaagagg aagtactgct atgactcatg cagcgaacaa cctttggacc tgtctatgaa   1020

gcgcccccgc gattaatcat taacctcaat aaacagcatg tgatgatgac tgattgtctg   1080

tgtctctgcc tatatatacc cttataagtg gtgcagggaa gggatgtggt gactgagcta   1140

ttcctcgagc tatcaatcat cgctcctgcc tttttt                             1176


<210> SEQ ID NO 6
<211> LENGTH: 30
<212> TYPE: DNA
<213> ORGANISM: Porcine adenovirus 4

<400> SEQUENCE: 6

ttttggatcc atgaagcggt ccgtcccgtc                                      30


<210> SEQ ID NO 7
<211> LENGTH: 31
<212> TYPE: DNA
<213> ORGANISM: Porcine adenovirus 4

<400> SEQUENCE: 7

ttttagatct ctacagtatc tgagggtaaa c                                    31


<210> SEQ ID NO 8
<211> LENGTH: 22
<212> TYPE: DNA
<213> ORGANISM: Porcine adenovirus 4

<400> SEQUENCE: 8

tttactgggc ttgtcgagac ag                                              22


<210> SEQ ID NO 9
<211> LENGTH: 20
<212> TYPE: DNA
<213> ORGANISM: Porcine adenovirus 4

<400> SEQUENCE: 9

gcactggact cggatggaca                                                 20


<210> SEQ ID NO 10
<211> LENGTH: 18
<212> TYPE: DNA
<213> ORGANISM: Porcine adenovirus 4

<400> SEQUENCE: 10

agctgcttgg tcctgcgt                                                   18


<210> SEQ ID NO 11
<211> LENGTH: 12
<212> TYPE: PRT
<213> ORGANISM: Porcine adenovirus 4

<400> SEQUENCE: 11

Cys Gly Gly Asp Phe Asp Pro Val Tyr Pro Tyr Asp
1               5                   10
```

<210> SEQ ID NO 12
<211> LENGTH: 14
<212> TYPE: PRT
<213> ORGANISM: Porcine adenovirus 4

<400> SEQUENCE: 12

Cys Ala Ala Ala Ser Glu Glu Met Pro Ala Pro Pro Glu Ala
1 5 10

<210> SEQ ID NO 13
<211> LENGTH: 460
<212> TYPE: PRT
<213> ORGANISM: Porcine adenovirus 3

<400> SEQUENCE: 13

Met Gly Pro Lys Lys Gln Lys Arg Glu Leu Pro Glu Asp Phe Asp Pro
1 5 10 15

Val Tyr Pro Tyr Asp Val Pro Gln Leu Gln Ile Asn Pro Pro Phe Val
20 25 30

Ser Gly Asp Gly Phe Asn Gln Ser Val Asp Gly Val Leu Ser Leu His
35 40 45

Ile Ala Pro Pro Leu Val Phe Asp Asn Thr Arg Ala Leu Thr Leu Ala
50 55 60

Phe Gly Gly Gly Leu Gln Leu Ser Gly Lys Gln Leu Val Val Ala Thr
65 70 75 80

Glu Gly Ser Gly Leu Thr Thr Asn Pro Asp Gly Lys Leu Val Leu Lys
85 90 95

Val Lys Ser Pro Ile Thr Leu Thr Ala Glu Gly Ile Ser Leu Ser Leu
100 105 110

Gly Pro Gly Leu Ser Asn Ser Glu Thr Gly Leu Ser Leu Gln Val Thr
115 120 125

Ala Pro Leu Gln Phe Gln Gly Asn Ala Leu Thr Leu Pro Leu Ala Ala
130 135 140

Gly Leu Gln Asn Thr Asp Gly Gly Met Gly Val Lys Leu Gly Ser Gly
145 150 155 160

Leu Thr Thr Asp Asn Ser Gln Ala Val Thr Val Gln Val Gly Asn Gly
165 170 175

Leu Gln Leu Asn Gly Glu Gly Gln Leu Thr Val Pro Ala Thr Ala Pro
180 185 190

Leu Val Ser Gly Ser Ala Gly Ile Ser Phe Asn Tyr Ser Ser Asn Asp
195 200 205

Phe Val Leu Asp Asn Asp Ser Leu Ser Leu Arg Pro Lys Ala Ile Ser
210 215 220

Val Thr Pro Pro Leu Gln Ser Thr Glu Asp Thr Ile Ser Leu Asn Tyr
225 230 235 240

Ser Asn Asp Phe Ser Val Asp Asn Gly Ala Leu Thr Leu Ala Pro Thr
245 250 255

Phe Lys Pro Tyr Thr Leu Trp Thr Gly Ala Ser Pro Thr Ala Asn Val
260 265 270

Ile Leu Thr Asn Thr Thr Thr Pro Asn Gly Thr Phe Phe Leu Cys Leu
275 280 285

Thr Arg Val Gly Gly Leu Val Leu Gly Ser Phe Ala Leu Lys Ser Ser
290 295 300

Ile Asp Leu Thr Ser Met Thr Lys Lys Val Asn Phe Ile Phe Asp Gly
305 310 315 320

Ala Gly Arg Leu Gln Ser Asp Ser Thr Tyr Lys Gly Arg Phe Gly Phe

```
                325                 330                 335

Arg Ser Asn Asp Ser Val Ile Glu Pro Thr Ala Ala Gly Leu Ser Pro
            340                 345                 350

Ala Trp Leu Met Pro Ser Thr Phe Ile Tyr Pro Arg Asn Thr Ser Gly
        355                 360                 365

Ser Ser Leu Thr Ser Phe Val Tyr Ile Asn Gln Thr Tyr Val His Val
    370                 375                 380

Asp Ile Lys Val Asn Thr Leu Ser Thr Asn Gly Tyr Ser Leu Glu Phe
385                 390                 395                 400

Asn Phe Gln Asn Met Ser Phe Ser Ala Pro Phe Ser Thr Ser Tyr Gly
            405                 410                 415

Thr Phe Cys Tyr Val Pro Arg Arg Thr Thr His Arg Pro Arg His Gly
            420                 425                 430

Pro Phe Ser Leu Arg Glu Arg Arg His Leu Phe Gln Leu Leu Gln Gln
        435                 440                 445

Cys Gly Gly Asp Phe Asp Pro Val Tyr Pro Tyr Asp
    450                 455                 460


<210> SEQ ID NO 14
<211> LENGTH: 703
<212> TYPE: PRT
<213> ORGANISM: Porcine adenovirus 4

<400> SEQUENCE: 14

Met Lys Arg Ser Val Pro Ser Asp Phe Asn Pro Val Tyr Pro Tyr Asp
1               5                   10                  15

Tyr Gln Pro Ile Ser Leu Met Pro Ala Phe Tyr Asp Asn Tyr Gly Phe
            20                  25                  30

His Glu Gly Pro Ser Gly Val Leu Ser Leu Asn Ile Ala Asn Pro Leu
        35                  40                  45

Gly Tyr Thr Pro Arg Lys Lys Leu Cys Leu Lys Leu Gly Glu Gly Leu
    50                  55                  60

Ala Leu Asp Ser Asp Gly His Leu Arg Val Gln Ile Pro Asp Met Gln
65                  70                  75                  80

Ala Gln Pro Pro Leu Leu Tyr Gln Gly His Arg Leu Ser Leu Leu Phe
                85                  90                  95

Asp Ala Asp Ala Gly Phe His Leu Thr Glu Asp Gly Ala Leu Ser Leu
            100                 105                 110

Thr Lys Thr Leu Val Tyr Pro Thr Leu Trp Thr Gly Pro Ala Pro Glu
        115                 120                 125

Ala Asn Val Thr Phe Ser Gly Glu Asn Ser Pro Ser Gly Ile Leu Arg
    130                 135                 140

Leu Cys Leu Ser Arg Thr Gly Gly Thr Val Ile Gly Thr Leu Ser Val
145                 150                 155                 160

Gln Gly Ser Leu Thr Asn Pro Ser Thr Gly Gln Thr Leu Gly Met Asn
                165                 170                 175

Leu Tyr Phe Asp Ala Asp Gly Asn Val Leu Ser Glu Ser Asn Leu Val
            180                 185                 190

Arg Gly Ser Trp Gly Met Lys Asp Gln Asp Thr Leu Val Thr Pro Ile
        195                 200                 205

Ala Asn Gly Gln Tyr Leu Met Pro Asn Leu Thr Ala Tyr Pro Arg Leu
    210                 215                 220

Ile Gln Thr Leu Thr Ser Ser Tyr Ile Tyr Thr Gln Ala His Leu Asp
225                 230                 235                 240

His Asn Asn Ser Val Val Asp Ile Lys Ile Gly Leu Asn Thr Asp Leu
```

-continued

```
                245                 250                 255

Arg Pro Thr Ala Ala Tyr Gly Leu Ser Phe Thr Met Thr Phe Thr Asn
            260                 265                 270

Ser Pro Pro Thr Ser Phe Gly Thr Asp Leu Val Gln Phe Gly Tyr Leu
        275                 280                 285

Gly Gln Asp Ser Ser Pro Ser Phe Leu Arg Glu Leu Pro Leu Ala Ser
    290                 295                 300

Glu Ala Gly Tyr Phe Gly Lys Leu Ala Ala Ala Ser Glu Glu Met Pro
305                 310                 315                 320

Ala Pro Pro Glu Ala Gln Thr Gln Asp Gln Ala Ala Glu Glu Pro Pro
                325                 330                 335

Ala Pro Ala Glu Ala Glu Ala Pro Ala Pro Ala Glu Ala Glu Ala Glu
            340                 345                 350

Ala Glu Pro Pro Arg Lys Pro Pro Arg Gly Asp Leu Ala Ala Leu Tyr
        355                 360                 365

Asn Arg Val His Ser Asp Thr Arg Ala Glu Asp Thr Pro Thr Ser Pro
    370                 375                 380

Glu Leu Val Thr Thr Leu Pro Asp Pro Phe Val Leu Pro Leu Pro Asp
385                 390                 395                 400

Gly Val Pro Thr Gly Ala Ser Ile Val Leu Glu Gly Thr Leu Thr Pro
                405                 410                 415

Ser Ala Val Phe Phe Thr Leu Asp Leu Val Thr Gly Pro Ala Ser Leu
            420                 425                 430

Ala Leu His Phe Asn Val Arg Leu Pro Leu Glu Gly Glu Lys His Ile
        435                 440                 445

Val Cys Asn Ser Arg Glu Gly Ser Ser Asn Trp Gly Glu Glu Val Arg
    450                 455                 460

Pro Gln Glu Phe Pro Phe Glu Arg Glu Lys Pro Phe Val Leu Val Ile
465                 470                 475                 480

Val Ile Gln Ser Asp Thr Tyr Gln Ile Thr Val Asn Gly Lys Pro Leu
                485                 490                 495

Val Asp Phe Pro Gln Arg Leu Gln Gly Ile Thr Arg Ala Ser Leu Ser
            500                 505                 510

Gly Asp Leu Val Phe Thr Arg Leu Thr Met Tyr Pro Pro Gly Asp Pro
        515                 520                 525

Arg Pro Thr Thr Leu Leu Pro Pro Pro Ala Ala Pro Leu Asp Val Ile
    530                 535                 540

Pro Asp Ala Tyr Val Leu Asn Leu Pro Thr Gly Leu Thr Pro Arg Thr
545                 550                 555                 560

Leu Leu Thr Val Thr Gly Thr Pro Thr Pro Leu Ala Glu Phe Phe Ile
                565                 570                 575

Val Asn Leu Val Tyr Asp Leu His Tyr Asp Ser Lys Asn Val Ala Leu
            580                 585                 590

His Phe Asn Val Gly Phe Thr Ser Asp Ser Lys Gly His Ile Ala Cys
        595                 600                 605

Asn Ala Arg Met Asn Gly Thr Trp Gly Ser Glu Ile Thr Val Ser Asp
    610                 615                 620

Phe Pro Phe Gln Arg Gly Lys Pro Phe Thr Leu Gln Ile Leu Thr Arg
625                 630                 635                 640

Glu Ala Asp Phe Gln Val Leu Val Asp Lys Gln Pro Leu Thr Gln Phe
                645                 650                 655

Gln Tyr Arg Leu Lys Glu Leu Asp Gln Ile Lys Tyr Val His Met Phe
            660                 665                 670
```

-continued

```
Gly His Val Val Gln Thr His Leu Glu His Gln Val Pro Asp Thr Pro
        675                 680                 685

Val Phe Ser Thr Ala Gly Val Ser Lys Val Tyr Pro Gln Ile Leu
    690                 695                 700
```

METHODS AND COMPOSITIONS FOR INCREASING TISSUE TROPISM OF RECOMBINANT ADENOVIRAL VECTORS

The present application is filed pursuant to 35 U.S.C. 371 as a U.S. National Phase application of International Patent Application No. PCT/IB07/02710, which was filed Jul. 27, 2007, claiming the benefit of priority to U.S. Provisional Patent Application No. 60/833,985, which was filed on Jul. 28, 2006. The entire text of the aforementioned applications is incorporated herein by reference in its entirety.

FIELD OF THE INVENTION

This invention relates to methods and compositions for increasing the tissue tropism of recombinant adenoviruses comprising using recombinant cells that provide to the recombinant adenovirus a second fibre, thereby altering the tropism of the recombinant adenovirus. The present invention also relates to methods of making and using recombinant adenoviruses having altered tropism.

BACKGROUND

The adenoviruses cause enteric or respiratory infection in humans as well as in domestic and laboratory animals. The adenovirus fibre protein plays an essential role in viral attachment by interacting with specific cellular receptors which facilitate entry into susceptible host cells. Thus the fibre protein determines the specific tissue tropism of a particular adenovirus (Chroboczek et al., 1995). The fibre is therefore considered the most important viral surface molecule in virion attachment to target cells.

In order to exploit this targeting property, several methods have been used to change the fibre protein carried by particular human adenoviruses. Several approaches have been undertaken to retarget adenovirus particles to different cell types, including the use of recombinant adenoviruses with modified fibre structure (Wickham et al., 1997; Dimitriev et al., 1998; Wirtz et al., 1999), single-chain antibodies (scFv) (Watkins et al., 1997; Douglas et al., 1999), chimeric fibre proteins (Krasnykh et al., 1996; Stevenson et al., 1997) and exchange of fibre proteins of different serotypes (Gall et al., 1996). These approaches either require the genetic manipulation of the adenovirus genome which reduces the already limited available space for incorporation of foreign genes into the viral genome, or complexing of bi-specific conjugates with adenovirus particles.

Using a different approach, Von Seggern, et al. (1998) constructed a cell line which stably expressed the Human Adenovirus serotype 5 (HAdV5) fibre protein. After passaging HAdV3 through this cell line, virus particles contained the serotype 5 fibre protein. Growth of a fibre defective mutant HAdV in this cell line allowed the generation of fibre positive Human adenovirus.

Additionally, cell lines expressing genes which enable complementation of adenoviral vectors with deletions in a number of regulatory genes have also been reported (Wang et al., 1995; Amalfitano et al., 1996; Amalfitano et al., 1997).

All the work thus far published on fibre-directed targeting appears to be focussed on re-directing the adenovirus from one specific target tissue type to another specific target tissue, and in some cases greatly restricting the target cells to which the adenovirus can attach. Additional methods are still needed to broaden the target tissue types in the animal to which the recombinant adenovirus can bind. Such methods may be useful in increasing or up-regulating either the amount and/or quality of the immune response generated against a particular antigen or the therapeutic effect of an immunomodulatory molecule.

SUMMARY OF THE INVENTION

The present invention exploits cell lines that express a fibre protein in order to provide the addition of a second fibre to a recombinant adenovirus vector without having to genetically insert the second fibre gene into the recombinant adenovirus genome. In so doing, these cells and methods of using the same allow for an increase in specific tissue tropism of a particular adenovirus. In addition, the fact that the second gene does not need to be genetically inserted into the recombinant adenovirus allows for greater room in the virus genome to be used for insertion of foreign genes.

The present invention thus provides in one aspect a recombinant adenoviral vector comprising an adenovirus that comprises a fibre gene native to the adenovirus and further comprises a second fibre gene that is heterologous to the adenovirus, wherein the second fibre gene is acquired by the recombinant adenovirus by growth of the recombinant adenovirus in a cell line that stably expresses the second fibre gene. The adenoviral vector may be any adenoviral vector, including but not limited to an adenoviral vector selected from the group consisting of porcine, human, avian, bovine equine and ovine adenovirus. Those skilled in the art are well aware that there are numerous serotypes of adenoviruses and it should be understood that the adenovirus vectors for the present invention need not be limited to any specific serotype. The invention particularly contemplates compositions that comprise the recombinant adenoviral vectors of the present invention. Such compositions preferably are pharmaceutical compositions that comprise a pharmaceutically acceptable excipient or diluent.

In specific embodiments, the adenovirus may be a recombinant porcine adenovirus selected from the group consisting of recombinant porcine adenovirus serotype (PAdV-1), recombinant PAdV-2, recombinant PAdV-3, recombinant PAdV-4, and recombinant PAdV-5, recombinant PAdV-6, and recombinant PAdV-7. Porcine adenovirus serotypes PAdV-1 to PAdV-5 are well known to those of skill in the art and have been well characterized. PAdV-6 and PAdV-7 also have been shown to exist and characterized by Kadoi (Kadoi et al., New Microbiol., 20:215-220, 1997; and Kadoi, New Microbiol., 20:89-91, 1997). In preferred embodiments, the recombinant adenoviral vector is a recombinant PAdV-3.

In other embodiments, the adenovirus is a recombinant HAdV, a recombinant bovine adenovirus (BAdV), a recombinant ovine adenovirus (OAdV), a recombinant murine adenovirus (MAdV), a recombinant simian adenovirus (SAdV), or a recombinant canine adenovirus (CAdV).

In specific recombinant adenoviral vectors of the invention, the second fibre protein is the fibre protein selected from PAdV-1, PAdV-2, PAdV-3, PAdV-4, and PAdV-5.

In certain aspects of the invention the recombinant adenoviral vector is an adenoviral vector (e.g., a PAdV-based vector) which further comprises a third fibre protein that is different from the first or the second fibre protein.

In preferred aspects, the second fibre protein in the recombinant vector comprises the fibre protein from PAdV-4.

The recombinant adenoviral vector of the invention may be replication competent or replication-defective. For example, the replication defective vector may be a recombinant PAdV that comprises a heterologous nucleotide sequence inserted into an essential region of the PAdV genome and the cell line that stably expresses the fibre gene also expresses the essential region of the PAdV genome into which the heterologous nucleotide sequence has been inserted.

Exemplary recombinant adenoviral vectors that are replication competent are those in which the recombinant adenovirus comprises a heterologous nucleotide sequence inserted into a non-essential region of the adenoviral genome. The heterologous nucleotide sequence may, in some embodiments be a heterologous gene that encodes a protein selected from the group consisting of an immunomodulator, an antigen, a pathogen, an immunogenic polypeptide, a therapeutic polypeptide, a growth hormone, and a cytokine.

Another aspect of the invention is directed to a host cell comprising an adenovirus that comprises a fibre gene native to the porcine adenovirus and wherein the host cell is a recombinant cell that expresses a fibre gene that is heterologous to the adenovirus and is capable of being infected by porcine adenovirus. The cell may be a mammalian cell or an avian cell. Exemplary mammalian cells include but are not limited to a porcine cell, a human cell, a bovine cell, and an ovine cell. In certain aspects, the cell is a recombinant porcine cell.

A further aspect of the invention relates to a composition capable of inducing an immune response in a mammalian subject, the composition comprising a recombinant adenoviral vector of the invention and a pharmaceutically acceptable excipient.

In other aspects, the invention describes methods of eliciting an immune response in a mammalian subject comprising administering such a composition to the mammalian subject. For example, the mammalian subject is a pig.

The invention also is directed to a method of preparing an adenovirus comprising culturing a recombinant host cell that expresses an adenoviral fibre gene under conditions suitable for infection of the cell with adenovirus, contacting the cell with a recombinant adenovirus vector which comprises the adenovirus sequence(s) essential for encapsidation and a heterologous gene that encodes a heterologous protein and wherein the recombinant adenovirus comprises a fibre gene that is different from the fibre gene in the host cell; and optionally harvesting the adenovirus. In specific embodiments, wherein the heterologous protein is a protein selected from the group consisting of an immunomodulator, an antigen, a pathogen, an immunogenic polypeptide, a therapeutic polypeptide, a growth hormone, and a cytokine.

In particular embodiments, this method is one in which the harvested adenovirus vector comprises a broader tissue specificity as compared to the adenovirus vector that is not contacted with the recombinant host cell.

Further, in the aforementioned method, the adenovirus vector may optionally be deleted in part or all of one or more adenoviral proteins that are non-essential for replication.

The invention also is directed to a vaccine for protecting a mammalian host against infection comprising the recombinant adenovirus vector of the invention and optionally a pharmaceutically acceptable excipient. In specific embodiments, the non-essential region is selected from the group consisting of the E3 region, ORF 1-2 and 4-7 of E4, the region between the end of E4 and the ITR of the porcine adenovirus genome.

Also described herein is a composition comprising a host cell that expresses an adenovirus fibre gene and a recombinant adenoviral vector that comprises nucleic acid that encodes a heterologous protein under the control of an expression control sequence, wherein the recombinant adenoviral vector comprises a fibre gene that is native to the adenovirus of the vector. In preferred aspects, the host cell has been infected with the recombinant porcine adenoviral vector.

The invention further relates to methods of treatment such as for example, methods of vaccinating an animal comprising administering to the animal a therapeutically effective amount of a vaccine described herein.

Other methods of the invention relate to increasing the host tissue cell specificity of a recombinant adenovirus vector comprising growing the recombinant adenovirus in a host cell that comprises a second fibre protein that is different from the fibre protein of the recombinant adenovirus. In such methods, the recombinant adenovirus vector may be a recombinant PAdV selected from the recombinant PAdV-1, recombinant PAdV-2, recombinant PAdV-3, recombinant PAdV-4, and recombinant PAdV-5. Preferably, the second fibre protein is the fibre protein selected from PAdV-1, PAdV-2, PAdV-3, PAdV-4, and PAdV-5. In the methods of the invention, the recombinant PAdV may further comprise a third fibre protein that is different from the first or the second fibre protein.

In preferred methods of increasing the host tissue cell specificity of a recombinant adenovirus vector, the recombinant PAdV used is a recombinant PAdV-3. In particular embodiments, such a recombinant PAdV-3 comprises the fibre protein from PAdV-4. In these methods, the recombinant PAdV may be replication competent or replication-defective. In particular preferred embodiments, the recombinant PAdV comprises a heterologous nucleotide sequence inserted into a non-essential region of the PAdV genome. In exemplary embodiments, the heterologous nucleotide sequence is a gene that encodes a protein selected from the group consisting of an immunomodulator, an antigen, a pathogen, an immunogenic polypeptide, a therapeutic polypeptide, a growth hormone, and a cytokine.

Other features and advantages of the present invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE DRAWINGS

The following drawings form part of the present specification and are included to further illustrate aspects of the present invention. The invention may be better understood by reference to the drawings in combination with the detailed description of the specific embodiments presented herein.

FIG. 4. The complete amino acid sequences of PAdV-3 and PAdV-4 fibre proteins and location of peptides. The sequences of the common and specific peptides used for generating rabbit anti-sera are highlighted in bold and underlined. (Reddy et al., 1995; Kleiboeker 1995).

DETAILED DESCRIPTION OF EXEMPLARY EMBODIMENTS OF THE PRESENT INVENTION

Figure 1:
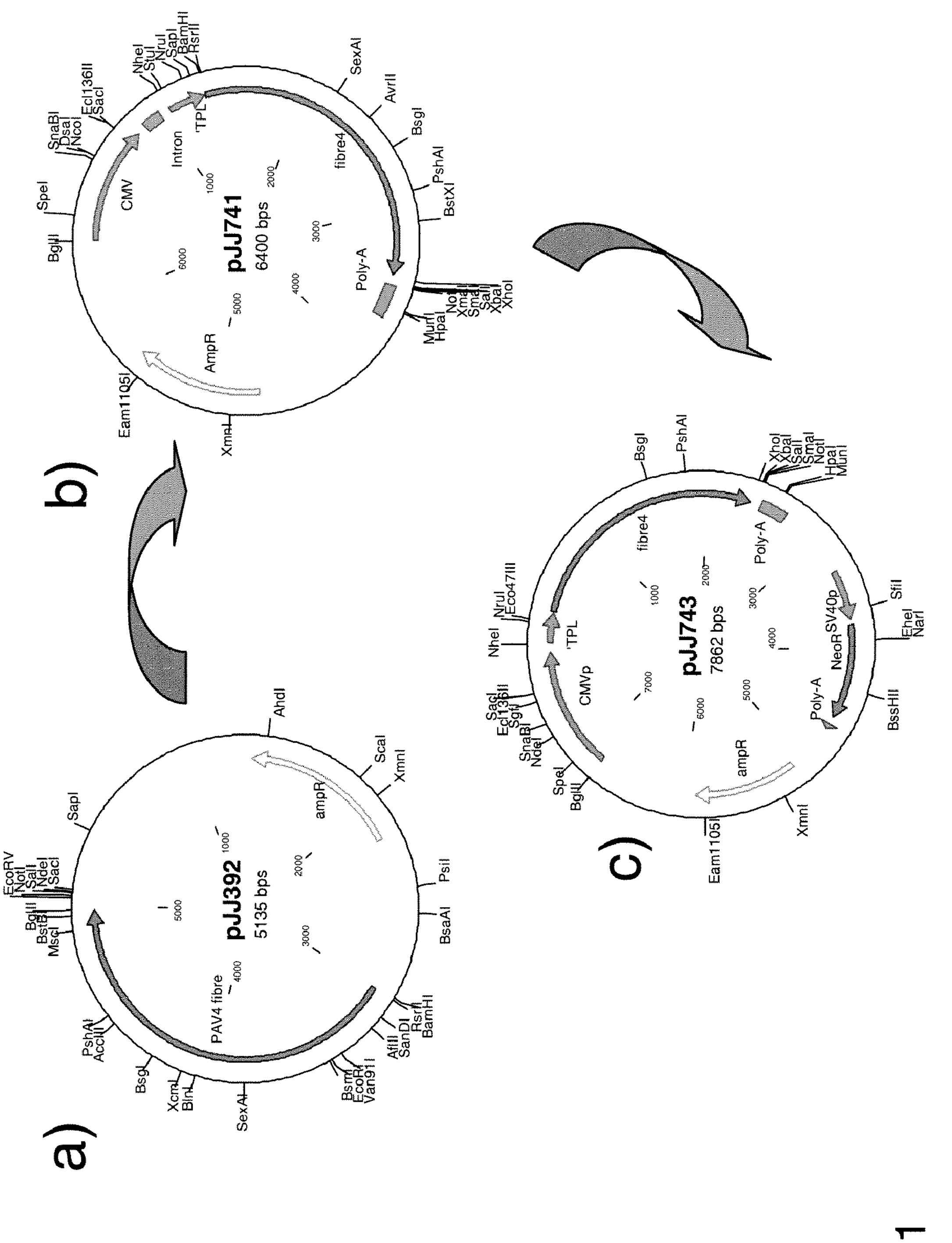
FIG. 1. Construction of plasmids containing the PAdV-4 fibre gene. a) The PAdV-4 fibre gene was amplified from PAdV-4 DNA by PCR and cloned into pGEM-T (Promega) resulting in plasmid PJJ392. b) The BamHI/BglII fragment from pJJ392 containing the PAdV-4 fibre gene was inserted into the BamHI site of plasmid pCI-PAdV-3 tripartite leader (TPL) downstream of the human cytomegalovirus immediate early promoter-enhancer (CMV) promoter and PAV-3 TPL sequence resulting in pJJ741. c) The transfer vector pJJ743 was constructed by inserting the NheI/NotI fragment of pJJ741 containing the PAdV-3TPL and PAdV-4 fibre gene into pCI-neo (Promega).

The present invention is related to the discovery and construction of improved adenovirus vectors. While the methods and compositions described herein are exemplified using porcine adenovirus vectors as model systems, it will readily be apparent that the methods of the present invention can readily be adapted for use in preparing recombinant adenoviral vectors that infect hosts other than pigs. The methods and compositions of the invention are used to alter the tropism of the recombinant adenoviral vector, thereby increasing the usefulness of the vector targeting it to tissues that it would not normally infect. In the present invention, a second fibre gene is provided to the recombinant adenovirus by growing the recombinant adenoviral vector in a cell line that expresses such a second fibre gene, wherein growth in such a cell line is associated with an alteration in the tropism of the recombinant adenoviral vector. The second fibre, contained in the cell line in which the recombinant adenovirus is propagated allows the adenovirus to infect the tissue for which the fibre gene in the cell line is specific. Methods and compositions for exploiting this finding are contemplated by the present invention.

The term “adenovirus vector” is used interchangeably with the term “adenoviral vector” herein. The adenovirus vectors employed herein are recombinant vectors that comprise a polynucleotide construct for the expression of a protein that is to be delivered by the adenoviral vector. The polynucleotide construct will preferably comprise DNA that encodes the protein to be delivered. Such DNA may be comprised of the nucleotide bases A, T, C, and G, but also may include any analogs or modified forms of such bases. Such analogs and modified bases are well known to those of skill in the art, and include but are not limited to methylated nucleotides, internucleotide modifications such as uncharged linkages and thioates, use of sugar analogs, and modified and/or alternative backbone structures, such as polyamides.

The adenovirus vectors used herein may be may be replication-competent or replication-defective in a target cell. In the event that the vectors are replication-defective, the vectors may require use of a helper cell or a helper virus to facilitate replication. Use of helper cells or helper viruses to promote replication of replication-defective adenoviral vectors is routine and well-known in the art. Typically, such helper cells provide the function of the entity that has been knocked out of the recombinant adenoviral vector to render it replication defective. A replication competent vector on the other hand may be referred to as a “helper-free virus vector” in that it does not require a second virus or a cell line to supply something defective in the vector.

As noted above, the present invention is used to alter the tropism of a given adenoviral vector, i.e., to change the specificity of an adenovirus. The term “altered tropism” encompasses changing species specificity as well as changing tissue or cell specificity of an adenovirus. In exemplary embodiments of the present invention, the specificity of an adenovirus vector is altered by providing to the vector a second fibre protein. The presence of two fibre proteins for the adenovirus vector achieves the desired alteration in the adenoviral vector tropism.

A. Fibre Genes

The present invention provides a second fibre to recombinant adenoviruses in order alter the tropism of those vectors. In preferred embodiments, the methods of the present invention comprise altering the tropism of a recombinant porcine adenoviral vector. PAdV infection has been associated with encephalitis, pneumonia, kidney lesions and diarrhea. (Derbyshire (1992) In: "Diseases of Swine" (ed. Leman et al.), 7th edition, Iowa State University Press, Ames, Iowa. pp. 225-227). Further, PAdV is capable of stimulating both humoral response and a mucosal antibody responses in the intestine of infected piglets. Tuboly et al. (1993) Res. in Vet. Sci. 54:345-350. There are at least 5 PAdV serotypes that have been described (PAdV-1, PAdV-2, PAdV-3, PAdV-4, PAdV-5; Derbyshire et al. (1975) J. Comp. Pathol. 85:437-443; and Hirahara et al. (1990) Jpn. J. Vet. Sci. 52:407-409.). Each of these serotypes can readily be used to prepare recombinant adenoviral vectors for use in for example, production of vaccines for pigs. The entire sequence of PAdV-3 has been cloned (Reddy et al., 1998; U.S. Pat. No. 6,492,343, incorporated herein by reference). In addition, there have been extensive characterizations of the genome of PAdDV-3 as well as PAdV-1 and PAdV-2 using restriction mapping and cloning of restriction fragments. See Reddy et al. (1993) Intervirology 36:161-168; Reddy et al. (1995b) Arch. Virol. 140:195-200.

Nucleotide sequences for various segments of various PAdV serotypes are well known to those of skill in the art. For example, PAdV-3 E3, pVIII and fibre genes are shown in Reddy et al. (1995) Virus Res. 36:97-106. PAdV-1 and PAdV-2 E3, pVIII and fibre genes are shown in Reddy et al. (1996) Virus Res. 43:99-109. Kleibocker provides the sequences of PAdV-4 E3, pVIII and fibre gene sequences (Kleiboeker 1994 Virus Res. 31:17-25). The PAdV-4 fibre gene sequence was determined by Kleiboeker (1995) Virus Res. 39:299-309. Inverted terminal repeat sequences for each of PAdV-1, PAdV-2, PAdV-3, PAdV-4, and PAdV-5 also are known in the art (Reddy et al (1995) Virology 212:237-239). The sequence of PAdV-3 penton was determined by McCoy et al. (1996) Arch. Virol. 141:1367-1375. The nucleotide sequence of the E1 region of PAdV-4 was shown in Kleiboeker (1995) Virus Res. 36:259-268. The sequence of the protease (23K) gene of PAdV-3 was determined by McCoy et al. (1996) DNA Seq. 6:251-254. The sequence of the PAdV-3 hexon gene (and the 14 N-terminal codons of the 23K protease gene) has been deposited in the GenBank database under accession No. U34592. The sequence of the PAdV-3 100K gene has been deposited in the GenBank database under accession No. U82628. The sequence of the PAdV-3 E4 region is known in the art (Reddy et al. (1997) Virus Genes 15:87-90.) Vrati et al. (1995, Virology, 209:400-408) disclose sequences for OAdV. The fibre and HNF-61 pVIII, ORF2, ORF3, ORF4 sequences for PAdV-5 are shown in Genbank accession no. AF186621. The complete genome sequence of PAdV-5 is shown at Genbank accession no. AC_000009 BK000411 in which the fibre gene is shown to be between 26487 . . . 27989, assigned to Genbank accession no. AP_000254. The complete sequence of porcine adenovirus C is given at Genbank accession no. NC_002702, in which the fibre gene is shown as being between 26487 . . . 27989 and assigned to Genbank accession no. NP_108675.1. A fibre sequence for PAdV-4 is shown in Genbank accession no. U25120.

Human adenoviruses HAdV-3, HAdV-4, HAdV-5, HAdV-9 and HAdV-35 are all well characterized in the art and are available from the American Tissue Culture Collection ATCC). The National Center for Biotechnology Information GenBank accession number for Ad5 is M73260/M29978; for Ad9 X74659; and for Ad35, U10272. Chow et al. (1977, Cell 12:1-8) disclose human adenovirus 2 sequences; Davison et al. (1993, J. Mole. Biol. 234:1308-1316) disclose the DNA sequence of HAdV-40; Sprengel et al. (1994, J. Virol. 68:379-389) disclose the DNA sequence for HAdV-12 DNA; Vrati et al. (1995, Virology, 209:400-408) disclose sequences for OAdV; Morrison et al. (1997, J. Gen. Virol. 78:873-878) disclose CAdV-1 DNA sequence; and Reddy et al. (1998, Virology, 251:414) disclose DNA sequences for PAdV. The fibre sequences of various human adenoviruses are available at GenBank under accession no. Y14241 (HAdV-28 fibre gene), Y14241 (HAdV-17 fibre gene;); a complete genome sequence for HAdV-17 is shown at the complete genome is at AC_000006 BK000406 in which the Fibre CDS is between 30935 . . . 32035, assigned Genbank accession no. AP_000157.1; X76706 (HAdV-15H9 (Morrison) fibre gene), X76548 (HAdV-31 gene for fibre protein); AB125751 (complete cds for HAdV-6 fibre gene), AB125750 (complete cds for HAdV-1 fibre gene), AB073168 (complete cds for HAdV-34 fibre gene); Genbank accession no. S75136 shows a sequence for the fibre gene of HAdV-8. The partial sequence of HAdV-3 fibre gene is deposited at Genbank accession no. AB244095, and the complete genome sequence of human adenovirus, given at Genbank accession no. DQ086466 which shows the fibre sequence being located at positions 31368 . . . 32327 which is assigned Genbank accession no. ABB17809.1. The complete sequence for HAdV-12 is shown at AC_000005 BK000405 in which the fibre gene CDS is at positions 29368 . . . 31131, assigned to Genbank accession no. AP_000135.1. The complete sequence of human adenovirus 5 is shown at Genbank accession no. AC_000008, in which the Fibre CDS is at 31042 . . . 32787, assigned to Genbank accession no. AP_000226.1. The complete sequence of human adenovirus 2 is shown at Genbank accession no. AC_000007 BK000407, in which the fibre cds is at 31030 . . . 32778, assigned to Genbank accession no. AP_000190.1. The sequence of HAdV-9 gene for fibre protein strain:130H is shown in Genbank accession no. AB098565. Another HAdV-9 fibre gene sequence is located at Genbank accession no. X74659. The fibre gene for HAdV-37 is shown at Genbank accession no. X94484. The fibre gene for HAdV-19 is shown at Genbank accession no. X94485. The fibre gene for HAdV-15 is shown at Genbank accession no. X72934. The fibre gene for a HAdV-7 (along with the E3 region) is shown in Genbank accession no. Z48954. A sequence for HAdV-4 fibre gene is shown in Genbank accession no. X76547. A sequence for HAdV-31 fibre gene is shown in Genbank accession no. X76548. A sequence for HAdV-8 fibre gene is shown in Genbank accession no. X74660. A sequence for HAdV-3, fibre gene is shown in Genbank accession no. X01998 M12411. A sequence for HAdV-21 fibre gene is shown in Genbank accession no. AY380332. A sequence for HAdV-7 fibre gene is shown in Genbank accession no. AY380326.

The simian adenovirus 1 complete genome is shown at Genbank accession no. NC_006879 in which the fibre is located at positions 28731 . . . 29822, and is assigned Genbank accession no. YP_213988.1 with a fibre 2 variant at Genbank accession no. YP_213989.1. The complete sequence of simian adenovirus A is given at Genbank accession no. NC_006144, with the fibre being located at 29606 . . . 31246 and assigned Genbank accession no. YP_067930. The complete genome sequence for simian adenovirus 25 is shown at Genbank accession no. AF394196 in which the fibre cds is 32137 . . . 33414 and assigned Genbank accession no. AAL35536.1.

Reddy et al. (1998) Journal of Virology 72:1394) disclose nucleotide sequences for BAdV-3. In that sequence, the penton regions of BAdV-3 starts at 12919 and ends at 14367; the hexon region starts at 17809 and ends at 20517; the fibre region of BAdV-3 starts at 27968 and ends at 30898. The fibre sequence and the sequence of bovine adenovirus type 3 pVIII gene, early region 3 and fibre protein has been deposited at GenBank under accession no. D16839. The complete genome of bovine adenovirus D is given at NC__002685 in which the fibre gene is annotated as being located between 22343 . . . 23950 and the fibre gene is given in Genbank accession no. NP__077404.1. Likewise, the complete genome for bovine adenovirus A is given at Genbank accession no. NC__006324 in which the fibre is located at positions 27483 . . . 29294 and depicted in Genbank accession no. YP__094049.1. The bovine adenovirus 4 strain THT/62, complete genome is shown at Genbank accession no. AF036092, with the fibre gene being located at positions 22343 . . . 23950 with an assigned Genbank no. of AAK13185.1. The complete sequence of BAdV-3 is shown at Genbank accession no. AC__000002 BK000401, in which the fibre cds is at 27968 . . . 30898, assigned to Genbank accession no. AP__000041.1. BAdV-2 fibre and 17K protein sequences are shown at AF308811.

The complete genome sequence for CAdV-1 is given at Genbank accession no. AC__000003 BK000402, in which the fibre cds is annotated as being at positions 25887 . . . 27518, with the protein and related coding sequence being deposited at Genbank accession no. AP__000069.1. The coding sequence for CAdV-2 is shown at Genbank accession no. AC__000020 BK000403, in which the fibre cds is annotated as being at positions 26592 . . . 28220, with the protein and related coding sequence being deposited at Genbank accession no. AP__000632.1. Genbank accession no. Z37498 shows the sequence of a CAdV-2 fibre gene.

The complete genome sequence for OAdV-7 is given at Genbank accession no. NC__004037, in which the fibre cds is annotated as being at positions 22273 . . . 23904, with the protein and related coding sequence being deposited at Genbank accession no. NP__659529.1.

The fibre sequence of feline adenovirus has been deposited at GenBank under accession no. AY518270.

Murine adenovirus A, complete genome is shown at Genbank accession no. NC__000942 in which the fibre gene cds is located at 25412 . . . 27253 and assigned Genbank accession no. NP__015554.1.

Genbank accession no. AC__000013 BK001451 shows the complete genome of fowl adenovirus 9 in which the fibre CDS is annotated as being at positions 30161 . . . 31876, with the protein and related coding sequence being deposited at AP__000390.1. FAdV-10 fibre sequence is shown at Genbank accession no. AF007579. Fowl adenovirus D complete genome is shown at Genbank accession no. NC__000899 in which the fibre gene cds is located at 30161 . . . 31876 and assigned Genbank accession no. NP__050293.1. Fowl adenovirus A complete genome is shown at Genbank accession no. NC__001720 in which the fibre gene CDS is located at 28363 . . . 30495 and assigned Genbank accession no. NP__043891.1. Turkey adenovirus 3, complete genome is shown at Genbank AC__000016 BK001454, with the fibre thereof being annotated to positions 22518 . . . 23882 and assigned Genbank accession no. AP__000495.1.

Frog adenovirus genome sequence is given at Genbank accession no. NC__002501 in which the fibre cds is located at positions 22343 . . . 23632, which is assigned Genbank accession no. NP__062452.1.

In particular exemplary embodiments, the present invention uses the fibre sequence from PAdV-4. The nucleotide sequence of a novel fibre-encoding sequence of PAdV-4 is given in SEQ ID NO:1. The nucleotide sequence of a novel fibre-encoding sequence from PAdV-1 is shown in SEQ ID NO:2. The nucleotide sequence of a novel fibre-encoding sequence from PAdV-2 is shown in SEQ ID NO:3.

As is readily apparent from the description above, those of skill in the art are aware of numerous coding sequences for fibre genes from a variety of adenovirus types. It should be understood that the invention herein is not limited to use any one of these fibre sequences. Indeed the methods and compositions of the invention can be conducted using any of the fibres mentioned above, any variants of those fibres as well as fibres identified from various other strains of adenoviruses. One skilled in the art will readily be able to identify such additional fibres through knowledge of the genome organization of the adenoviruses and through knowledge of the exemplified sequences discussed above. In this regard, it is noted that in U.S. Patent Publication No. 20020034519 (incorporated herein by reference in its entirety), FIGS. 12-17 thereof are of particular note as showing the sequence of various fibre proteins, including HAdV-5 fibre protein (FIG. 12 therein), BAdV-3 (FIG. 13 therein) ovine Adenovirus 287 fibre protein (FIG. 14 therein); PAdV-3 fibre protein (FIG. 15 therein); CAdV-2 fibre protein (FIG. 16 therein); and FIGS. 17A-17G depicting an amino acid alignment of mammalian adenovirus fibre regions using the clustal method of the multialign program.

In the present invention in exemplary embodiments, a recombinant adenoviral vector that has been prepared through conventional methods used for the preparation of recombinant adenoviral vectors is propagated in a cell line that is recombinant cell line that expresses a fibre gene that is different from the fibre gene that is present in the recombinant adenovirus. It should be understood that while the recombinant adenovirus preferably contains the fibre gene that is associated with that serotype (e.g., if the recombinant adenovirus is a PAdV-3-based recombinant adenovirus, then the fibre gene in that recombinant adenovirus is the native PAdV-3 fibre gene) it will also be possible to use the present invention to alter the tropism of recombinant adenoviruses in which the native fibre gene has been modified (e.g., replaced by a fibre of another adenovirus, or mutated to be different from the native-wild-type fibre gene.)

As used herein, the term "propagate" is used interchangeably with "replicate" and refers to the ability of the adenovirus vector to reproduce or proliferate. These terms are well understood in the art. As used herein, replication involves production of adenovirus proteins and is generally directed to reproduction of adenovirus vector. Replication can be measured using assays standard in the art and described herein, such as a burst assay or plaque assay. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

In exemplary embodiments, part or all of a second fibre protein-encoding encoding polynucleotide sequence is expressed in a recombinant host cell in which the adenoviral vector is to be propagated. Propagation of the recombinant adenoviral vector in that host cell alters the adenovirus tropism. In a particular embodiment disclosed herein, recombinant cells that express the PAdV-4 fibre gene are prepared. In exemplary embodiments, cell lines stably expressing the PAdV-4 fibre gene were generated. The PAdV-3 fibre facilitates virus attachment to cells in the gut of pigs whereas the PAdV-4 serotype fibre allows attachment to porcine respiratory tract cells. An existing porcine adenovirus recombinant vector that expresses the gp55 gene of CSFV [Hammond et al., 2000] could be grown in these cell lines with the resulting progenitor virus containing both the native PAdV-3 fibre and the additional PAdV-4 fibre protein. The presence of two different fibre proteins on the viral capsid would broaden the cellular tropism of the vector. Thus enabling the vector to target a greater variety of cell types within the animal and expose the delivered foreign gene to a greater breadth of host immune responses. Furthermore, PAdV vectors engineered to have the fibre gene deleted to provide more space for the insertion of foreign genes could be complemented by passaging them through these cell lines expressing the fibre protein. This approach would allow the production of fibre positive virus with additional DNA packaging capability.

It is expected that growth of recombinant PAdV's through such cell lines will increase the efficacy of the vectors by broadening their host cell target range and increase the amount of foreign genetic material that can be inserted into them, thus allowing the incorporation and subsequent delivery of several antigens, or antigens plus immunomodulators such as cytokines, in one vector.

A "host cell" is a cell which has been transformed, or is capable of transformation, by an exogenous DNA sequence. In the present invention, the host cells are those that can support the replication of an adenoviral vector (i.e., can become infected by the adenovirus and allow the adenovirus to replicate therein) and have been transformed by an exogenous DNA sequence that encodes all or part of a fibre protein. "Transformation" of a cell entails introduction of exogenous DNA into the cell. While it is understood that the exogenous DNA may or may not be integrated (covalently linked) to chromosomal DNA making up the genome of the cell, in the present invention, cells are stably transformed with the fibre-encoding polynucleotide. A stably transformed cell is one in which the exogenous DNA has become integrated into the chromosome so that it is inherited by daughter cells through chromosome replication. For mammalian cells, this stability is demonstrated by the ability of the cell to establish cell lines or clones comprised of a population of daughter cell containing the exogenous DNA.

In exemplary embodiments, the present invention provides examples of stably transformed porcine cells that have been stably transformed with exogenous DNA that encodes PAdV-4 fibre. More particularly, two exemplary continuous (stable) cell lines, pig kidney 15 (PK15) and swine testis (ST) were engineered to contain and express the fibre gene from PAdV-4. These cell lines were named PK-743 and ST-743 respectively. The Fibre gene was shown to be expressed by demonstration of the presence of PAdV-4 fibre mRNA in both cell lines. Western blot analysis using either rabbit polyclonal antibody raised against a peptide common to both fibres or against a peptide specific to PAdV-4 fibre clearly demonstrated the presence of both fibres in modified virus. The cell lines were used in infection studies in which PK15A (unmodified control) and PK-743 (modified) cells were infected with the recombinant PAdV-3-gp55 and progeny virus harvested when cells were showing 80% cytopathic effect.

Progeny virus can be analysed using standard techniques known to those of skill in the art. For example, Western blot analysis of the protein content of progeny virus demonstrated the presence of both the PAdV-3 and PAdV-4 fibre proteins in the virion. A band of the expected molecular weight for the PAdV-3 fibre (45 kD) was present in both preparations of virus whereas a band of the expected molecular weight of the PAdV-4 fibre (77 kD) was specifically detected in the modified virus preparation.

While the present invention provides exemplary porcine host cells, other suitable host cells can readily be prepared and will include any cell that will support recombination between an adenoviral genome and the adenoviral fibre in the host cell. The host cells are transfected with a plasmid containing the recombinant adenoviral genome, to generate virus particles in those host cells. The growth of eukaryotic cells and mammalian cell lines are procedures which are well-known to those of skill in the art.

As noted above, preparation of the recombinant adenoviral vector will employ techniques well known to those of skill in the art. Using such techniques, one or more heterologous polynucleotide sequences are inserted into one or more regions of the adenoviral genome to generate a recombinant adenoviral vector. The preparation of these vectors is limited only by the insertion capacity of the given adenoviral genome and ability of the recombinant adenoviral vector to express the inserted heterologous sequences. In general, adenovirus genomes can accept inserts that increase the size of the recombinant adenovirus to be approximately 105% of the wild-type genome length and remain capable of being packaged into virus particles. The insertion capacity can be increased by deletion of non-essential regions and/or deletion of essential regions, such as, for example, E1 function, whose function can then be provided by a helper cell line, such as one providing E1 function. In some embodiments, a heterologous polynucleotide encoding a protein is inserted into an adenovirus E3 gene region. In other embodiments, the non-essential portions of the E3 region are deleted and the heterologous polynucleotide encoding a protein is inserted at that gap left by the deletion. In some preferred embodiments, where the recombinant adenoviral vector is a PAdV-3 based adenoviral vector, the heterologous gene can be inserted into the region of the PAdV-3 genome located after the polyadenylation signal for PAdV-3 E3 and before the start of the ORF for the PAdV-3 fibre gene.

In some embodiments, an adenovirus is created where the insertion or the deletion followed by the insertion is in the E1 gene region of the adenovirus the vector is then propagated in a helper cell line providing E1 function. Other regions into which the heterologous gene may be inserted include the E4 region. Where the recombinant adenoviral vector is a PAdV-3 based vector, the entire E4 region, except that region that encodes ORF3 can be deleted to make room for the heterologous gene. As shown in Li et al. (Virus Research 104 (2004) 181-190), the PAdV-3 E4 region located at the right-hand end of the genome is transcribed in a leftward direction and has the potential to encode seven (p1-p7) ORFs. Of these only ORF p3 is essential for the replication. As such, much if not all of the rest of the E4 region may readily be deleted without rendering the virus replication defective, thereby allowing for more room for heterologous inserts.

In one embodiment of the invention, insertion can be achieved by constructing a plasmid containing the region of the adenoviral genome into which insertion is desired, such as a polynucleotide encoding for a desired therapeutic protein. The plasmid is then digested with a restriction enzyme having a recognition sequence in that adenoviral portion of the plasmid, and a heterologous polynucleotide sequence is inserted at the site of restriction digestion. The plasmid, containing a portion of the adenoviral genome with an inserted heterologous sequence, is co-transformed, along with an adenoviral genome or a linearized plasmid containing the adenoviral genome into a bacterial cell (such as, for example, *E. coli*). Homologous recombination between the plasmids generates a recombinant adenoviral genome containing inserted heterologous sequences. In these embodiments, the adenoviral genome can be a full-length genome or can contain one or more deletions as discussed herein.

Deletion of adenoviral sequences, for example to provide a site for insertion of heterologous sequences or to provide additional capacity for insertion at a different site, can be accomplished by methods well-known to those of skill in the art. For example, for adenoviral sequences cloned in a plasmid, digestion with one or more restriction enzymes (with at least one recognition sequence in the adenoviral insert) followed by ligation will, in some cases, result in deletion of sequences between the restriction enzyme recognition sites. Alternatively, digestion at a single restriction enzyme recognition site within the adenoviral insert, followed by exonuclease treatment, followed by ligation will result in deletion of adenoviral sequences adjacent to the restriction site. A plasmid containing one or more portions of the adenoviral genome with one or more deletions, constructed as described above, can be co-transfected into a bacterial cell along with an adenoviral genome (full-length or deleted) or a plasmid containing either a full-length or a deleted genome to generate, by homologous recombination, a plasmid containing a recombinant genome with a deletion at one or more specific sites. Adenoviral virions containing the deletion can then be obtained by transfection of mammalian cells including but not limited to the stably transformed cells containing the additional fibre gene described herein, with the plasmid containing the recombinant adenoviral genome.

The insertion sites may be adjacent to and transcriptionally downstream of endogenous promoters in the adenovirus. An "endogenous" promoter, enhancer, or control region is native to or derived from adenovirus. Restriction enzyme recognition sequences downstream of given promoters that can be used as insertion sites, can be easily determined by one of skill in the art from knowledge of part or all of the sequence of adenoviral genome into which the insertion is desired. Alternatively, various in vitro techniques are available to allow for insertion of a restriction enzyme recognition sequence at a particular site, or for insertion of heterologous sequences at a site that does not contain a restriction enzyme recognition sequence. Such methods include, but are not limited to, oligonucleotide-mediated heteroduplex formation for insertion of one or more restriction enzyme recognition sequences (see, for example, Zoller et al. (1982) Nucleic Acids Res. 10:6487-6500; Brennan et al. (1990) Roux's Arch. Dev. Biol. 199:89-96; and Kunkel et al. (1987) Meth. Enzymology 154:367-382) and PCR-mediated methods for insertion of longer sequences. See, for example, Zheng et al. (1994) Virus Research 31:163-186.

Expression of a heterologous sequence inserted at a site that is not downstream from an endogenous promoter also can be achieved by providing, with the heterologous sequence, a transcriptional regulatory sequences that are active in eukaryotic cells. Such transcriptional regulatory sequences can include cellular promoters such as, for example, the viral promoters such as, for example, herpesvirus, adenovirus and papovavirus promoters and DNA copies of retroviral long terminal repeat (LTR) sequences. In such embodiments, the heterologous gene is introduced in an expression construct in which the heterologous gene is operatively linked to such transcriptional regulatory elements.

In specific exemplary embodiments, PAdV-4 fibre gene was placed under the control of the CMV promoter in order to provide strong constitutive transcription. It desirable to have fibre production continue during virus packaging which occurs during the late phase of viral infection. It has been shown that human adenoviruses shut off host cell protein synthesis by inactivating a host cell translation initiation factor (Zhang et al., 1994). Efficient translation of late viral messages was therefore expected to be maintained by the inclusion of the PAdV-3 TPL sequence. The TPL is composed of three exons totalling 248 nucleotides (nt) which are spliced onto the 5' end of late viral mRNAs (Reddy et al., 1998). The sequence is thought to function by providing a less ordered structure at the 5' end of the mRNA, conferring independence from the host cell initiation complex (Dolph et al., 1988; Dolph et al., 1990). In order to ensure continued translation of the recombinant fibre mRNA, the PAdV-4 fibre gene was placed downstream of the PAdV-3 TPL sequence in pCI-TPL. Addition of the HAdV 5 TPL to constructs expressing luciferase has been reported to increase levels of expression even in uninfected cells (Sheay et al., 1993).

Regulatory sequences which can be used to regulate the expression of heterologous genes, can for example be, a transcriptional regulatory sequence, a promoter, an enhancer, an upstream regulatory domain, a splicing signal, a polyadenylation signal, a transcriptional termination sequence, a translational regulatory sequence, a ribosome binding site and a translational termination sequence.

It should be understood that preparation of the recombinant adenoviral vectors includes propagation of the cloned adenoviral genome as a plasmid and rescue of the infectious virus from plasmid-containing cells.

The presence of viral nucleic acids can be detected by techniques known to one of skill in the art including, but not limited to, hybridization assays, polymerase chain reaction, and other types of amplification reactions. Similarly, methods for detection of proteins are well-known to those of skill in the art and include, but are not limited to, various types of immunoassay, ELISA, Western blotting, enzymatic assay, immunohistochemistry, etc. Diagnostic kits comprising the nucleotide sequences of the invention may also contain reagents for cell disruption and nucleic acid purification, as well as buffers and solvents for the formation, selection and detection of hybrids. Diagnostic kits comprising the polypeptides or amino acid sequences of the invention may also comprise reagents for protein isolation and for the formation, isolation, purification and/or detection of immune complexes.

The present invention provides for modification of recombinant adenoviral vectors to alter their tropism. Those vectors preferably are used to deliver various foreign genes or nucleotide sequences or coding sequences (prokaryotic, and eukaryotic) to a target cell. Such vectors are particularly useful as vaccines to provide protection against a wide range of diseases and many such genes are already known in the art. The viral vaccines include, but are not limited to, DNA vaccines (i.e., using plasmids, vectors or other conventional carriers to directly inject DNA into pigs), live vaccines, modified live vaccines, inactivated vaccines, subunit vaccines, attenuated vaccines, genetically engineered vaccines, etc.

The exogenous (i.e., foreign) nucleotide sequence that is incorporated into the adenovirus can consist of one or more gene(s) of interest or other nucleotide sequences that are not genes but have other functions, and preferably of therapeutic interest. In the context of the present invention, a nucleotide sequence or gene of interest can code either for an antisense RNA, short hairpin RNA, a ribozyme or for an mRNA which will then be translated into a protein of interest. Such a nucleotide sequence or gene may comprise genomic DNA, complementary DNA (cDNA) or of mixed type (minigene, in which at least one intron is deleted). The nucleotide sequence or gene can encode a regulatory or therapeutic function, a mature protein, a precursor of a mature protein, in particular a precursor that comprises a signal peptide, a chimeric protein originating from the fusion of sequences of diverse origins, or a mutant of a natural protein displaying improved or modified biological properties. Such a mutant may be obtained by, deletion, substitution and/or addition of one or more nucleotide(s) of the gene coding for the natural protein, or any other type of change in the sequence encoding the natural protein, such as, for example, transposition or inversion.

The gene that is being delivered by the vector may be placed under the control of elements (DNA control sequences) suitable for its expression in a host cell. Suitable DNA control sequences are understood to mean the set of elements needed for transcription of a gene into RNA (antisense RNA or mRNA) and for the translation of an mRNA into protein. For example, these elements would include at least a promoter. The promoter may be a constitutive promoter or a regulatable promoter, and can be isolated from any gene of eukaryotic, prokaryotic or viral origin, and even adenoviral origin. Alternatively, it can be the natural promoter of the gene of interest. Generally speaking, a promoter used in the present invention may be modified so as to contain regulatory sequences. Exemplary promoters may include tissue specific promoters when the gene is to be targeted to a given tissue type. Other conventional promoters that may be used include but are not limited to the HSV-1 TK (herpesvirus type 1 thymidine kinase) gene promoter, the adenoviral MLP (major late promoter), the RSV (Rous Sarcoma Virus) LTR (long terminal repeat), the CMV immediate early promoter, SV-40 immediate early promoter, and the PGK (phosphoglycerate kinase) gene promoter, for example, permitting expression in a large number of cell types.

The genes to be delivered by the adenoviral vectors may be any genes including but not limited to genes that encode cytokines such as interferons and interleukins; genes encoding lymphokines; genes coding for membrane receptors such as the receptors recognized by pathogenic organisms (viruses, bacteria or parasites), preferably by the HIV virus (human immunodeficiency virus); genes coding for coagulation factors such as factor VIII and factor IX; genes coding for dystrophins; genes coding for antigenic epitopes in order to increase the host cell's immunity; genes coding for major histocompatibility complex classes I and II proteins, as well as the genes coding for the proteins which are inducers of these genes; genes coding for antibodies; genes coding for immunotoxins; genes encoding toxins; genes encoding growth factors or growth hormones; genes encoding cell receptors and their ligands; genes encoding tumor suppressors; genes involved in cardiovascular disease including, but not limited to, oncogenes; genes encoding growth factors including, but not limited to, fibroblast growth factor (FGF), vascular endothelial growth factor (VEGF), and nerve growth factor (NGF); e-nos, tumor suppressor genes including, but not limited to, the Rb (retinoblastoma) gene; lipoprotein lipase; superoxide dismutase (SOD); catalase; oxygen and free radical scavengers; apolipoproteins; and pai-1 (plasminogen activator inhibitor-1); genes coding for cellular enzymes or those produced by pathogenic organisms; and suicide genes.

In certain preferred embodiments the vaccines of the present invention are prepared to vaccinate swine against causing diseases in those animals. For example, the vaccines may be directed to pseudorabies virus (PRV) gp50; transmissible gastroenteritis virus (TGEV) S gene; porcine rotavirus VP7 and VP8 genes; genes of porcine respiratory and reproductive syndrome virus (PRRS), in particular ORFs 3, 5 and 7; genes of porcine epidemic diarrhea virus; genes of hog cholera virus; genes of porcine parvovirus; and genes of foot-and-mouth disease virus; genes associated with porcine circovirus; and genes of porcine influenza virus. Representative bovine pathogen antigens include bovine herpes virus type 1; bovine diarrhea virus; bovine coronavirus; and genes of foot-and-mouth disease virus. Representative human pathogen antigens include but are not limited to HIV virus antigens and hepatitis virus antigens.

Cytokines and growth factors such as vascular endothelial growth factor (VEGF), epidermal growth factor, fibroblast growth factor, pleiotrophin, platelet-derived growth factor, erythropoietin, stem-cell factor (SCF), TNF-α; an interferon such as interferon-γ, interferon β, interferon-α, granulocyte-colony-stimulating-factor (G-CSF) granulocyte-macrophage colony stimulating factor (GM-CSF); stromal cell-derived factor-1, macrophage colony stimulating factor, RANTES, IGF-1, SDF-1, MIP1α, MCP-1 and MCP-2, eotaxin, eotaxin3, eotaxin4, LKN1, MPIF-2 and LD78beta, Leukemia Inhibitory Factor (LIF) interleukins such as e.g., IL-1, IL2, IL-3, IL4, IL-5, IL-6, IL-7, IL-8. IL-9, IL10, IL-11, IL-12, IL-13, IL-14, IL-15, IL-16, IL-17, IL-18, IL-19, IL-20, IL-21, IL-22, IL-23, IL-24, IL-25, TOLL-like receptors and ligands, integrin receptors, and the like also may be delivered using the vectors of the present invention.

It should be understood that while in some circumstances it might be desirable to incorporate the whole gene into the vector, other vectors can be constructed that comprise only a portion of the nucleotide sequences of genes can be used (where these are sufficient to generate a protective immune response or a specific biological effect) rather than the complete sequence as found in the wild-type organism. Where the genes contain a large number of introns, a cDNA may be preferred.

As noted above, the gene may be inserted under the control of a suitable promoter. In addition the vector also may comprise enhancer elements and polyadenylation sequences. Promoters and polyadenylation sequences which provide successful expression of foreign genes in mammalian cells and construction of expression cassettes, are known in the art, for example in U.S. Pat. No. 5,151,267, the disclosures of which are incorporated herein by reference.

The term "expression cassette" refers to a natural or recombinantly produced nucleic acid molecule that is capable of expressing a gene or genetic sequence in a cell. An expression cassette typically includes a promoter (allowing transcription initiation), and a sequence encoding one or more proteins or RNAs. Optionally, the expression cassette may include transcriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include translation termination signals, a polyadenosine sequence, internal ribosome entry sites (IRES), and non-coding sequences. Optionally, the expression cassette may include a gene or partial gene sequence that is not translated into a protein. The nucleic acid can effect a change in the DNA or RNA sequence of the target cell. This can be achieved by hybridization, multi-strand nucleic acid formation, homologous recombination, gene conversion, RNA interference or other yet to be described mechanisms The adenoviral vectors may comprise more than one foreign gene. The methods of the invention can be used to provide protection against a wide variety of diseases affecting pigs, humans, cattle, and other mammals. Any of the recombinant antigenic determinants or recombinant live viruses of the invention can be formulated and used in substantially the same manner as described for antigenic determinant vaccines or live vaccine vectors.

While exemplary embodiments of the present invention are such that the heterologous nucleotide (also referred to herein in as heterologous nucleic acid) is one which encodes a protein, it should be understood that the heterologous nucleotide may in fact be any polynucleotide containing a sequence whose presence or transcription in a cell is desired. Thus the vectors may be used to delivery any polynucleotide that, for example, causes sequence-specific degradation or inhibition of the function, transcription, or translation of a gene. Such heterologous nucleotides may be selected from the group comprising: siRNA, microRNA, interfering RNA or RNAi, dsRNA, ribozymes, antisense polynucleotides, and DNA expression cassettes encoding siRNA, microRNA, dsRNA, ribozymes or antisense nucleic acids. SiRNA comprises a double stranded structure typically containing 15-50 base pairs and preferably 19-25 base pairs and having a nucleotide sequence identical or nearly identical to an expressed target gene or RNA within the cell. An siRNA may be composed of two annealed polynucleotides or a single polynucleotide that forms a hairpin structure. MicroRNAs (mRNAs) are small noncoding polynucleotides, about 22 nucleotides long, that direct destruction or translational repression of their mRNA targets. Antisense polynucleotides comprise sequence that is complimentary to a gene or mRNA. Antisense polynucleotides include, but are not limited to: morpholinos, 2'-O-methyl polynucleotides, DNA, RNA and the like. Such heterologous nucleotide sequences may be polymerized in vitro, recombinant, contain chimeric sequences, or may be derivatives of these groups. These sequences may may contain ribonucleotides, deoxyribonucleotides, synthetic nucleotides, or any suitable combination such that a target RNA and/or a gene is inhibited.

In exemplary embodiments, modified rPAdV-gp55 was grown in PK15-743 cells, or rPAdV-gp55 grown in un-modified PK15A cells. It was then administered to commercially available Large White Pigs by sub-cutaneous or oral routes. The modified vaccine completely protected pigs from lethal challenge with CSFV when given as sub-cutaneous injection or by the oral route. In addition, the modified vaccine given by the sub-cutaneous route generated the highest levels of NPLA antibodies, greater than those detected in the unmodified vaccine group. Previous work has demonstrated that when the unmodified vaccine is given by the oral route, no NPLA antibody titre can be detected before challenge, even following a booster dose [Hammond et al., 2001; Hammond et al., 2003]. However, very significant levels of NPLA antibodies were detected in the oral group after only a single dose of the modified vaccine, and these levels were boosted by the administration of a second dose. This is evidence that the modified vaccine containing both the PAdV-3 and PAdV-4 fibre proteins is being targeted to a wider variety of tissues in the pig than the unmodified vaccine, and as a consequence is generating a more extensive immune response in the host.

Specifically contemplated herein are pharmaceutical compositions comprising a therapeutically effective amount of a recombinant adenovirus vector, recombinant adenovirus or recombinant protein, prepared according to the methods of the invention, in combination with a pharmaceutically acceptable vehicle and/or an adjuvant. Such a pharmaceutical composition can be prepared and dosages determined according to techniques that are well-known in the art. The pharmaceutical compositions of the invention can be administered by any known administration route including, but not limited to, systemically (for example, intravenously, intratracheally, intravascularly, intrapulmonarilly, intraperitoneally, intranasally, parenterally, enterically, intramuscularly, subcutaneously, intratumorally or intracranially), by oral administration, by aerosolization or intrapulmonary instillation. Administration can take place in a single dose or in doses repeated one or more times after certain time intervals. The appropriate administration route and dosage will vary in accordance with the situation (for example, the individual being treated, the disorder to be treated or the gene or polypeptide of interest), but can be determined by one of skill in the art.

The invention further provides for methods of treatment in which a therapeutically effective amount of a recombinant adenoviral vector (e.g., a PAdV-3 adenoviral vector) that has altered tropism as compared to the recombinant vector that has not been propagated in a cell line that contains a fibre gene is administered to a mammalian subject requiring treatment.

The antigens used in the present invention can be either native or recombinant antigenic polypeptides or fragments. They can be partial sequences, full-length sequences, or even fusions (e.g., having appropriate leader sequences for the recombinant host, or with an additional antigen sequence for another pathogen). The preferred antigenic polypeptide to be expressed by the virus systems of the present invention contain full-length (or near full-length) sequences encoding antigens. Alternatively, shorter sequences that are antigenic (i.e., encode one or more epitopes) can be used. The shorter sequence can encode a "neutralizing epitope," which is defined as an epitope capable of eliciting antibodies that neutralize virus infectivity in an in vitro assay. Preferably the peptide should encode a "protective epitope" that is capable of raising in the host a "protective immune response;" i.e., an antibody- and/or a cell-mediated immune response that protects an immunized host from infection.

The antigens used in the present invention, particularly when comprised of short oligopeptides, can be conjugated to a vaccine carrier. Vaccine carriers are well known in the art: for example, bovine serum albumin (BSA), human serum albumin (HSA) and keyhole limpet hemocyanin (KLH).

Genes for desired antigens or coding sequences thereof which can be inserted include those of organisms which cause disease in mammals, particularly bovine pathogens such as foot-and-mouth disease virus, bovine rotavirus, bovine coronavirus, bovine herpes virus type 1, bovine respiratory syncytial virus, bovine parainfluenza virus type 3 (BPI-3), bovine diarrhea virus, *Pasteurella haemolytica, Haemophilus somnus* and the like. Genes encoding antigens of human pathogens also useful in the practice of the invention. The vaccines of the invention carrying foreign genes or fragments can also be orally administered in a suitable oral carrier, such as in an enteric-coated dosage form. Oral formulations include such normally-employed excipients as, for example, pharmaceutical grades of mannitol, lactose, starch, magnesium stearate, sodium saccharin cellulose, magnesium carbonate, and the like. Oral vaccine compositions may be taken in the form of solutions, suspensions, tablets, pills, capsules, sustained release formulations, or powders, containing from about 10% to about 95% of the active ingredient, preferably about 25% to about 70%. Oral and/or intranasal vaccination may be preferable to raise mucosal immunity (which plays an important role in protection against pathogens infecting the respiratory and gastrointestinal tracts) in combination with systemic immunity.

In addition, the vaccine can be formulated into a suppository. For suppositories, the vaccine composition will include traditional binders and carriers, such as polyalkaline glycols or triglycerides. Such suppositories may be formed from mixtures containing the active ingredient in the range of about 0.5% to about 10% (w/w), preferably about 1% to about 2%.

Protocols for administering to animals the vaccine composition(s) of the present invention are within the skill of the art in view of the present disclosure. Those skilled in the art will select a concentration of the vaccine composition in a dose effective to elicit an antibody and/or T-cell mediated immune response to the antigenic fragment or another type of therapeutic or prophylactic effect. Within wide limits, the dosage is not believed to be critical. Typically, the vaccine composition is administered in a manner which will deliver between about 1 to about 1,000 micrograms of the subunit antigen in a convenient volume of vehicle, e.g., about 1-10 cc. Preferably, the dosage in a single immunization will deliver from about 1 to about 500 micrograms of subunit antigen, more preferably about 5-10 to about 100-200 micrograms (e.g., 5-200 micrograms).

The timing of administration may also be important. For example, a primary inoculation preferably may be followed by subsequent booster inoculations if needed. It may also be preferred, although optional, to administer a second, booster immunization to the animal several weeks to several months after the initial immunization. To insure sustained high levels of protection against disease, it may be helpful to readminister a booster immunization to the animals at regular intervals, for example once every several years. Alternatively, an initial dose may be administered orally followed by later inoculations, or vice versa. Preferred vaccination protocols can be established through routine vaccination protocol experiments.

The dosage for all routes of administration of in vivo recombinant virus vaccine depends on various factors including, the size of host/patient, nature of infection against which protection is needed, carrier and the like and can readily be determined by those of skill in the art. By way of non-limiting example, a dosage of between $10^3$ pfu and $10^{15}$ pfu, preferably between $10^4$ and $10^{13}$ pfu, more preferably between $10^5$ to $10^{11}$ pfu and the like can be used. As with in vitro subunit vaccines, additional dosages can be given as determined by the clinical factors involved.

In some embodiments of the invention, recombinant cell lines are produced by constructing an expression cassette comprising a fibre region, e.g., the fibre region of PADV-4 as shown in the examples, and transforming host cells therewith to provide the cells that contain the second fibre gene for the purposes of the present invention to alter the tropism of the recombinant adenoviruses. These recombinant cell lines are capable of allowing a second fibre to be inserted into the adenoviral vector. These cell lines are also extremely useful in generating recombinant vectors, having a fibre gene deletion replaced by heterologous nucleotide sequence encoding for a foreign gene or fragment, by in vivo recombination following DNA-mediated cotransfection. In addition, the host cells also may provide one or more essential functions encoded for the adenoviral genome, wherein the cell line provides a function or functions that is (are) lacking in a particular defective recombinant adenoviral vector. Thus the recombinant cell lines that contain the fibre also may be complementing cell lines that can provide viral functions through, for example, co-infection with a helper virus, or by integrating or otherwise maintaining in stable form a fragment of a viral genome encoding a particular viral function.

The recombinant mammalian, particularly porcine, cell lines of the invention could also be used for the recombinant production of proteins.

The invention also includes a method for providing gene delivery to a mammal, such as a porcine, bovine, human, ovine, canine, feline, or other mammal in need thereof, to control a gene deficiency, to provide a therapeutic gene or nucleotide sequence and/or to induce or correct a gene mutation. The method can be used, for example, in the treatment of conditions including, but not limited to hereditary disease, infectious disease, cardiovascular disease, and viral infection. These kinds of techniques are currently being used by those of skill in the art for the treatment of a variety of disease conditions. Examples of foreign genes, nucleotide sequences or portions thereof that can be incorporated for use in a conventional gene therapy include, cystic fibrosis transmembrane conductance regulator gene, human minidystrophin gene, alpha-1-antitrypsin gene, genes involved in cardiovascular disease, and the like.

In particular, the practice of the present invention in regard to gene delivery in humans is intended for the prevention or treatment of diseases including, but not limited to, genetic diseases (for example, hemophilia, thalassemias, emphysema, Gaucher's disease, cystic fibrosis, Duchenne muscular dystrophy, Duchenne's or Becker's myopathy, etc.), cancers, viral diseases (for example, AIDS, herpesvirus infection, cytomegalovirus infection and papillomavirus infection), cardiovascular diseases, and the like. For the purposes of the present invention, the vectors, cells and viral particles prepared by the methods of the invention may be introduced into a subject either ex vivo, (i.e., in a cell or cells removed from the patient) or directly in vivo into the body to be treated.

EXAMPLES

In the present examples there are provided exemplary teachings of methods and compositions for the production of cell lines stably expressing the PAdV-4 fibre gene. Existing porcine adenovirus recombinant vectors, e.g., PAdV-3 vectors that express the gp55 gene of classical swine fever virus (CSFV) [Hammond et al., 2000] could be grown in these cell lines with the resulting progenitor virus containing both the native PAdV-3 fibre and the additional PAdV-4 fibre protein. The presence of two different fibre proteins on the viral capsid broadens the cellular tropism of the vector. In so doing, the vector is able to target a greater variety of cell types within the animal and expose the delivered foreign gene to a greater breadth of host immune responses. Furthermore, the recombinant vectors can be engineered to have the fibre gene deleted to provide more space for the insertion of foreign genes could be complemented by passaging them through these cell lines expressing the fibre protein. This approach would allow the production of fibre positive virus with additional DNA packaging capability.

Example 1

Materials and Methods

Cells & Viruses: Porcine kidney cells (PK-15) obtained from American Type Culture Collection number CCL-33 (ATCC-CCL-33) were grown in Earle's modified Eagles medium (EMEM) supplemented with 5% foetal calf serum (FCS), 10 mM N-2-Hydroxyethylpiperazine-N'-2-ethanesulfonic acid (HEPES), 1% Na-pyruvate and 2 mM glutamine. Swine testes cells (ST) from the United States Department of Agriculture-Animal and Plant Health Inspection Services (USDA-APHIS) were maintained in EMEM supplemented with 10% FCS, 10 mM HEPES, 1% Na-pyruvate, 0.25% lactalbumine hydrolysate (LAH) and 2 mM glutamine.

Porcine adenovirus was grown in primary porcine kidney (1° PK) cells maintained in EMEM supplemented with 2% FCS and harvested when 90% of the cells showed cytopathic effect (CPE). All media were further supplemented with 2.5 μg/ml fungizone (Squibb), 100 units/ml penicillin and 100 μg/ml streptomycin (CSL).

Virus DNA preparation: Virus DNA was prepared by the method of Hirt (1967) with minor modifications as described by Shinagawa et al. (1983) and restriction enzyme digests were carried out according to the manufacturers' instructions.

Plasmid DNA preparation: Plasmid DNA was prepared using the Qiagen system according to the manufacturer's instructions.

Isolation of PAdV-4 fibre gene from PAdV-4 DNA: The PADV-4 fibre gene was amplified from PAdV-4 DNA by PCR using the primer pair:

```
PADV-4 5' TTTTGGATCCATGAAGCGGTCCGTCCCGTC length 30
              BamHI

PADV-4 3' TTTTAGATCTCTACAGTATCTGAGGGTAAAC length 31
              BglII
```

PCR was carried out using PCR supermix (Life technologies) in an extension protocol of 30 cycles of 94° C. 1 minute, 50° C. 2 minutes and 72° C. 30 seconds with a 30 second extension each cycle.

Plasmid Constructs: The PAdV-4 fibre PCR product was gel purified and ligated into pGEM-T (Promega) to give the plasmid PJJ392 (FIG. 1*a*). Following restriction enzyme digestion, a BamHI/BglII fragment from pJJ392 containing the PAdV-4 fibre gene was inserted into the BamHI site of plasmid pCI-TPL to yield pJJ741 (FIG. 1*b*). The transfer vector pJJ743 was then constructed by inserting an NheI/NotI fragment of pJJ741 containing the TPL-PADV-4 fibre gene into pCIneo (Promega) (FIG. 1*c*). Plasmid constructs were checked for the presence of the correct insert by restriction enzyme digests and confirmed by sequencing using the primer 5' TTT ACT GGG CTT GTC GAG ACA G 3' which binds 5' of the TPL sequence.

Production and Characterization of Stable Cell Lines: ST and PK-15 cells were grown in their respective media and approximately $5\times10^6$ cells were electroporated with 20 μg XmnI linearised plasmid pJJ743 DNA, using a Bio-Rad Genepulser at settings of 300 V, 960 μF and ∞Ω. Cells were left to recover overnight in their respective media supplemented with 1.25% DMSO (Melkonyan et al., 1996). G418 resistant cells were then selected with the addition of either 800 (ST) or 1000 (PK15) μg/ml G418 (Promega) to cultures. Individual clones were isolated by limiting dilutions and expanded. Clones were screened for presence of fibre genes by PCR and expression of fibre mRNA confirmed by RT-PCR.

Purification of genomic DNA: Genomic DNA from transfected cells was purified using the DNeasy Tissue Kit (Qiagen) according to the manufacturer's instructions.

PCR conditions and primers: PCR was carried out using PCR supermix (Gibco BRL) in a standard protocol of 1 cycle at 94° C. for 10 minutes, 30 cycles of 94° C. 1 minute, 50° C. 1 minute and 72° C. 2 minutes and a final extension at 72° C. for 10 minutes. Primer pair 5' GCA CTG GAC TCG GAT GGA CA and 3' AGC TGC TTG GTC CTG CGT CT 3' were used in the detection of the PADV-4 fibre gene with an expected band of 804 bp.

RT-PCR Purification of cellular mRNA: Total RNA from transfected cells was purified using the RNeasy Mini Kit (Qiagen) according to the manufacturer's instructions.

RT-PCR First strand cDNA synthesis: mRNA was converted into cDNA using the SUPERSCRIPT Preamplification System for First Strand cDNA Synthesis (Gibco BRL) according to the manufacturer's instruction.

RT-PCR Amplification of target cDNA: The target cDNA was amplified using the PCR protocol and primers described above Production of rPAdV-gp55 stock: PK15A, PK15-743, ST and ST-743 cells were cultured to 90% confluency before infection with rPAdV-gp55. 200 μl of rPAdVgp55 was added to the cell sheet and was adsorbed at 37° C. for 1 h. 20 ml of EMEM (supplemented with 2% final concentration FCS) was added. Flasks were incubated at 37° C. in 5% $CO_2$ and observed daily for cpe. When flasks showed 70-80% cpe virus was harvested by freeze/thawing three times.

Preparation of purified virus stock: The supernatant from each group of flasks was pooled and clarified by centrifuging for 20 min at 2000 rpm in a Jouan C3000 bench centrifuge. The supernatant was then decanted into SW28 ultracentrifuge tubes and centrifuged for 90 min at 25,000 rpm at 20° C. in a Beckman LM-80 ultracentrifuge. The supernatant was discarded and viral pellets resuspended in 500 μl TE. Material was stored at ⁻20° C. in 1.5 ml screw cap tubes (Sarstedt) until required.

Purification using a discontinuous sucrose density gradient: Crude virus preparations were further purified using a discontinuous sucrose gradient prepared in SW28 ultra centrifuge tubes comprising 3 concentrations of sucrose at 60% (w/v), 30% (w/v) and 20% (w/v) in NTE. One ml of the viral stock was carefully layered onto the gradient and tubes were centrifuged at 28,000 rpm for 2 h at 4° C. in a Beckman LM-80 ultracentrifuge. Purified virus was removed using a 5 ml syringe and 19 gauge needle and placed into an SW28 ultracentrifuge tube which was then filled with TE. Purified virus was then pelleted in a Beckman LM-80 ultracentrifuge for 90 min at 25,000 rpm at 20° C. to remove the sucrose. Pellets were finally resuspended in TE and stored at ⁻20° C. until required.

Generation of fibre specific peptide rabbit antisera: The amino acid sequences of PAdV-3 and PAdV-4 fibre proteins (Reddy et al., 1995; Kleiboeker 1995) were compared and two synthetic peptides (Auspep Pty Ltd-Australia) were designed and generated. Peptide 1 comprised a region of the fibre protein that was conserved between PAdV-3 and PAdV-4 and peptide 2 comprised a sequence specific to PAdV-4 fibre.

PAdV-3/PAdV-4 common peptide: CGG<u>DFDPVYPYD</u>

PAdV-4 specific peptide: C<u>AAASEEMPAPPEA</u>

Figure 5:
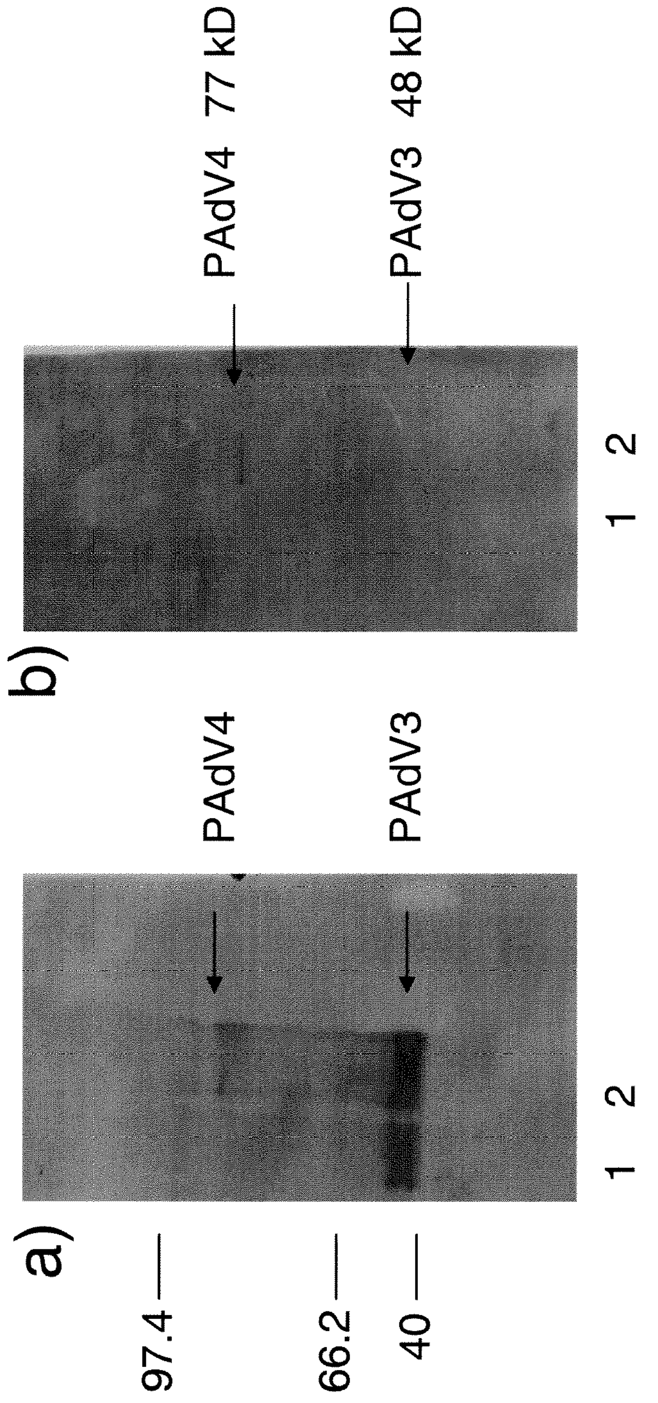
FIG. 5. Demonstration of PAdV-3 and PAdV-4 fibres in modified vaccine. Recombinant PAdV-glycoprotein 55 (gp55) was grown in PK15A cells (unmodified) or PK743 cells (modified). Proteins present in duplicate virus samples were separated by SDS/PAGE, blotted onto nitrocellulose and stained with either a rabbit antibody raised against a common fibre peptide (panel a) or against a PAdV-4 specific fibre peptide (panel b). Lane 1=unmodified virus, lane 2=modified virus. High range molecular weight markers, position and approximate molecular weight of fibre proteins are shown.

The complete amino acid sequences of PAdV-3 and PAdV-4 fibre proteins and the locations of the 2 peptides are shown in FIG. 5. In order to generate an immune response in rabbits both peptides were conjugated to KLH (keyhole limpet haemocyanin). Both peptide conjugates were injected into rabbits to produce specific antisera as shown in table 1.

TABLE 1

Rabbits were bled before any treatment on each date. 2 female white rabbits were given the specific peptide in adjuvant and 2 female white rabbits were given the common peptide in adjuvant. The adjuvant used for the first two doses was Quil A and the adjuvant used for the remaining doses was IFA (incomplete Freunds adjuvant) 1 ml total of peptide (4 × 250 μl) in adjuvant was administered via the sub-cutaneous route. On day 113 rabbits were bled out and the sera was separated and stored at $^{-}20°$ C. until required.

| Day | Bled and Given Peptide | Adjuvant | Amount of Peptide |
|---|---|---|---|
| 0 | + | QuilA | 4 × 50 μg/ml |
| 22 | + | QuilA | 4 × 50 μg/ml |
| 34 | + | IFA | 4 × 50 μg/ml |
| 44 | + | IFA | 4 × 50 μg/ml |
| 70 | + | IFA | 4 × 50 μg/ml |
| 89 | + | IFA | 4 × 50 μg/ml |
| 99 | + | IFA | 4 × 50 μg/ml |
| 113 | Final Bleed | N/A | N/A |

Examination of purified virus for the presence of PAdV-4 fibre: SDS-PAGE gel analysis. Samples of purified virus were analysed for the presence of PADV-3 and PADV-4 fibre proteins on 8-12% Bis-Tris SDS-PAGE precast gels (Invitrogen). Following electrophoresis, proteins were transferred onto nitrocellulose membranes by immuno-blotting for 1 h at 100 V. Membranes were then blocked in TBS/3% bovine serum albumin at 4° C. overnight.

Examination of purified virus for the presence of PAdV-4 fibre: Western blot analysis. All washes and antibody incubations were carried out at room temperature. Membranes were washed twice for 5 min in TBS-Tween/Triton and once for 10 min with TBS. Polyclonal rabbit anti-fibre antibody at a 1/200 dilution in TBS/3% BSA was added to the membranes which were then incubated for 1 h. Membranes were washed for 2×5 min in TBS-Tween/Triton and once for 10 min in TBS. Membranes were then incubated with goat anti-rabbit conjugated to horse-radish peroxidase (HRP) (Sigma) at a 1/500 dilution in a 5% skimmed milk/blotto solution. Membranes were then washed as above and protein bands visualised using enhanced chemiluminescence (ECL) detection (Amersham Pharmacia Biotech Ltd).

In vivo analysis using Pig Experiments. Modified rPAdV-gp55 grown in PK15-743 cells, or rPAdV-gp55 grown in un-modified PK15A cells, was administered to commercially available Large White Pigs using the following regime:

Day 0: All pigs bled and vaccinated

Group 1: $1^{st}$ dose—$2\times10^5$ $TCID_{50}$ unmodified rPAdV-gp55 vaccine by sub-cutaneous injection.

Group 2: $1^{st}$ dose—$2\times10^5$ $TCID_{50}$ modified rPAdV-gp55 by sub-cutaneous injection.

Group 3: $1^{st}$ dose—$2\times10^5$ $TCID_{50}$ modified rPAdV-gp55 by the oral route.

Day 22:

Group 1: $2^{nd}$ booster dose—$2\times10^5$ $TCID_{50}$ unmodified rPAdV-gp55 vaccine by sub-cutaneous injection.

Group 2: $2^{nd}$ booster dose—$2\times10^5$ $TCID_{50}$ modified rPAdV-gp55 vaccine by sub-cutaneous injection.

Group 3: $2^{nd}$ booster dose—$2\times10^5$ $TCID_{50}$ modified rPAdV-gp55 by the oral route.

Day 47: Two clean age and weight matched pigs were brought in as challenge virus controls.

Day 49: All pigs including clean controls, were challenged with a lethal dose of CSFV 'Weybridge' strain (1000 $TCID_{50}$) by sub-cutaneous injection. Rectal temperatures were recorded daily following challenge and all pigs monitored daily for clinical signs of disease manifested as loss of appetite, recumbency, diarrhoea and reddening above the feet. Pigs were euthanased at the end of the experiment or when showing severe clinical disease and spleens were removed for CSFV antigen detection. Post mortem examinations were carried out on all euthanased pigs.

Detection of Serum Neutralising Antibodies against CSFV: Pigs were bled at weekly intervals and sera tested for the presence of neutralising antibodies against CSFV by neutralising peroxidase-linked assay (NPLA) as described by Terpstra and colleagues, [1984]. NPLA titres were expressed as the reciprocal of the serum dilution that neutralised 200 $TCID_{50}$ of the Weybridge strain in 50% of the replicate cultures.

Antigen Capture ELISA: The presence of CSFV antigen in the spleens of challenged pigs was determined by antigen capture ELISA [Shannon et al.,1993].

Example 2

Results Preparation of Vectors, Cell lines and Virus

Generation of the transfer vector containing the PAdV-4 fibre Nucleotide sequencing confirmed that the transfer vector pJJ743 contained the PAdV-4 fibre gene downstream of the PAdV-3 TPL sequence (FIG. 1*c*).

Figure 2:
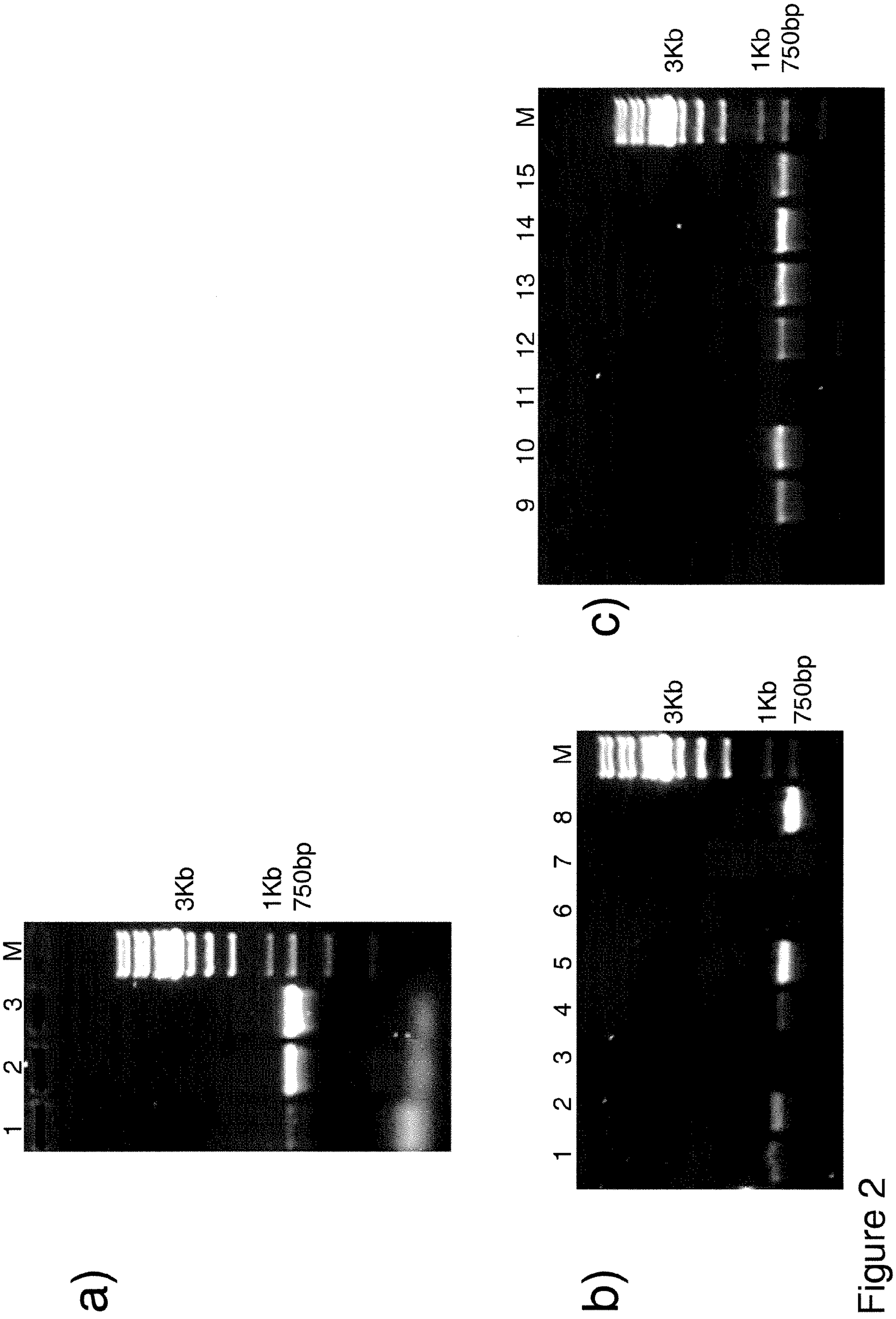
FIG. 2. PCR detection of PAdV-4 fibre DNA in cell lines. Genomic DNA from transfected cells was purified and tested by PCR for the presence of the PAdV-4 fibre gene. a) lane 1=PK15 clone 8, lane 2=PK15 clone 9, lane 3=pJJ743 control, M=1 Kb DNA ladder. b) lanes 1-5=ST clones 2-6, lane 6 untransfected ST DNA, lane 7 PADV-4 DNA, lane 8 pJJ743 control. c) lanes 9-15=ST clones 7-14, M=1 Kb DNA ladder.

Generation of cell lines constitutively expressing the PAdV-4 fibre protein: ST and PK-15 cells were transfected with the transfer vector pJJ743 followed by selection with G418 to establish clones containing integrated DNA. Two PK-15 clones (8 and 9) were tested were shown by PCR to contain the PAdV-4 fibre gene (FIG. 2*a*). Twelve ST clones transfected with pJJ743 (2-14) were tested by PCR and 10 (2,3,5,6,7,8 and 11-14) were shown to contain the PAdV-4 fibre gene (FIGS. 2*b* and *c*). Positive clones were then named with the cell type followed by the pre-fix 743 and the clone number i.e. PK15-743-9.

Expression of fibre mRNA in these cell clones was then evaluated by RT-PCR.

Figure 3:
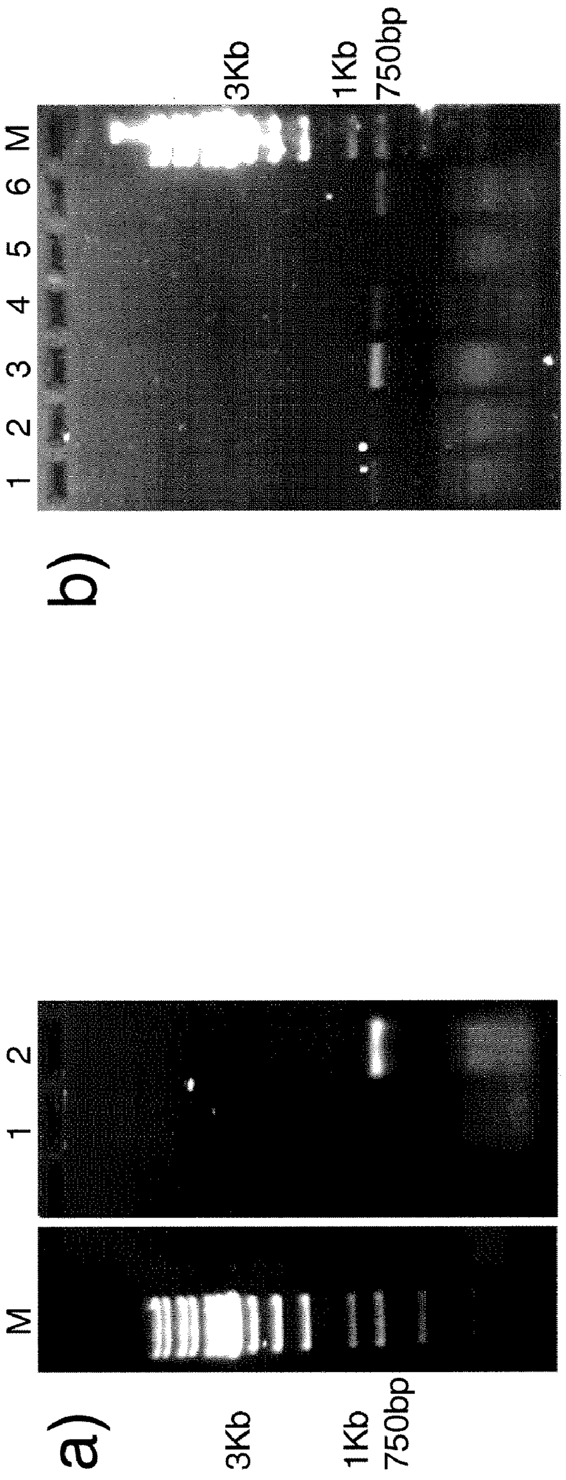
FIG. 3. Reverse transcription PCR (RT-PCR) detection of PAdV-4 fibre mRNA from cell lines. Total RNA from transfected cells was prepared and those clones positive by PCR for the PAdV-4 fibre gene were tested for the synthesis of PAdV-4 fibre mRNA by RT-PCR. a) lane 1=PK15 clone 8, lane 2=PK15 clone 9, M=1 Kb DNA ladder. b) lanes 1-6=ST clones 2,3,5,6,7 and 8, M=1 Kb DNA ladder.

Large quantities of fibre 4 mRNA were detected in cell lines PK15-743-9 and ST-743-2,5,6 and 8 (FIGS. 3*a* and *b*).

Growth characteristics: Following insertion of the fibre gene both PK-15-743 and ST 743 cells grew more slowly than the parent lines.

Examination of purified virus for the presence of PAdV-4 fibre: Cell line PK15-743-9 was infected with rPAdV-gp55 and virus harvested when cells were showing 80% cpe. Virus was purified and samples were separated on 8-12% SDS-PAGE gels. Following transfer to nylon membranes samples were analysed by western blot for the presence of PAdV-3 and PAdV-4 fibre proteins using rabbit anti-serum raised against the two peptides described above.

When treated with the peptide anti-sera raised against the common epitope of PAdV 3 and 4 fibres, a doublet of bands corresponding to the expected molecular weight (45 kD) of the PAdV-3 fibre could be seen in the lane containing rPAdV-gp55 grown in un-modified PK15 cells (FIG. 5*a* lane 1). In contrast, the lane containing rPAdV-gp55 grown in modified PK15-743-9 cells contained a doublet corresponding to the PAdV-3 fibre, and also an additional band at the expected molecular weight (77 kD) of the PAdV-4 fibre (FIG. 5*a* lane 2). When treated with the peptide anti-sera raised against the specific epitope on the PAdV-4 fibre, no bands were detected in the lane containing rPAdV-gp55 grown in un-modified PK15 cells (FIG. 5*b* lane 1) whereas a single band at the expected molecular weight of the PAdV-4 fibre was seen in the lane containing rPAdV-gp55 grown in modified PK15-743-9 cells (FIG. 5*b* lane 2).

Example 3

Results Pig Vaccination Studies

Pig trial to test the efficacy of rPAdV-gp55 with modified fibre profile In order to test the efficacy of the modified rPAdV-gp55 vaccine containing both the PAdV-3 and PAdV-4 serotype fibres, groups of Large White pigs were given two doses of either un-modified or modified vaccine and their susceptibility to lethal challenge with CSFV determined. In addition, the ability of the modified vaccine to induce neutralising antibody and to give protection when administered by the oral route was tested.

Pig reaction to vaccination: There were no adverse effects on pigs following vaccination of either vaccine preparation by either route. There were no increases in body temperature or appearance of clinical signs.

Figure 6:
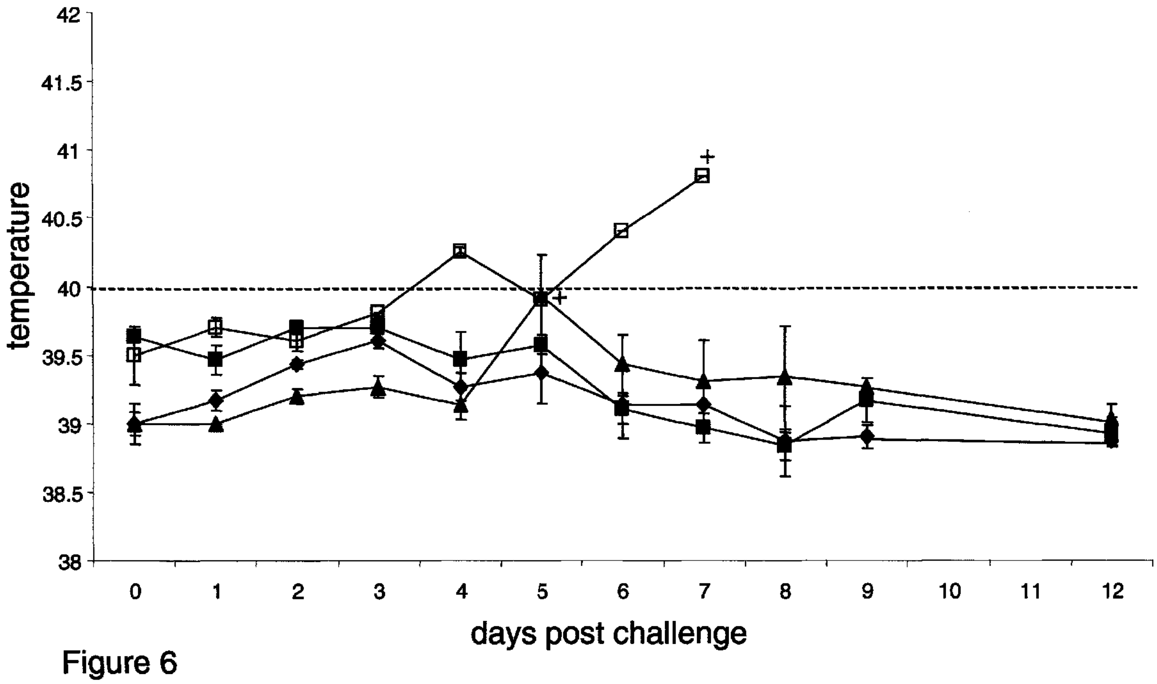
FIG. 6. Temperatures of pigs post challenge. Pigs were vaccinated on day 0 and given a booster dose on day 22. Pigs were challenged on day 49 with Classical swine fever virus (CSFV). Rectal temperatures of each pig were measured daily following CSFV challenge. The mean temperatures and standard error bars for each group of pigs are shown. ♦=Unmodified rPAdV-gp55 s/c, ■=Modified rPAdV-gp55 s/c, ▲=Modified rPAdV-gp55 oral, □=Controls, +=euthanased.

Pig temperatures post challenge: The mean daily temperature and standard error for the control pigs and each group of vaccinated pigs is shown in FIG. 6.

Control pigs: Control pigs developed fever and showed clinical signs of CSF by day 4 with one pig dying overnight on day 4-5 and one pig euthanased with severe disease on day 7-post challenge (p.c.).

Group 1: None of the pigs given sub-cutaneous doses of unmodified rPAdV-gp55 developed fever nor showed any clinical signs of CSF up to the termination of the experiment.

Group 2: None of the pigs given sub-cutaneous doses of modified rPAdV-gp55 developed fever nor showed any clinical signs of CSF up to the termination of the experiment.

Group 3: Two out of 3 pigs given the oral doses of modified rPAdV-gp55 did not develop fever nor show any clinical signs of CSF up to the termination of the experiment. One pig presented a temperature above 40° C. on 2 separate, non-successive days, but displayed no other clinical signs of CSF up to the termination of the experiment. Importantly, the mean temperature of the group did not rise above 40° C. during the challenge period.

Figure 7:
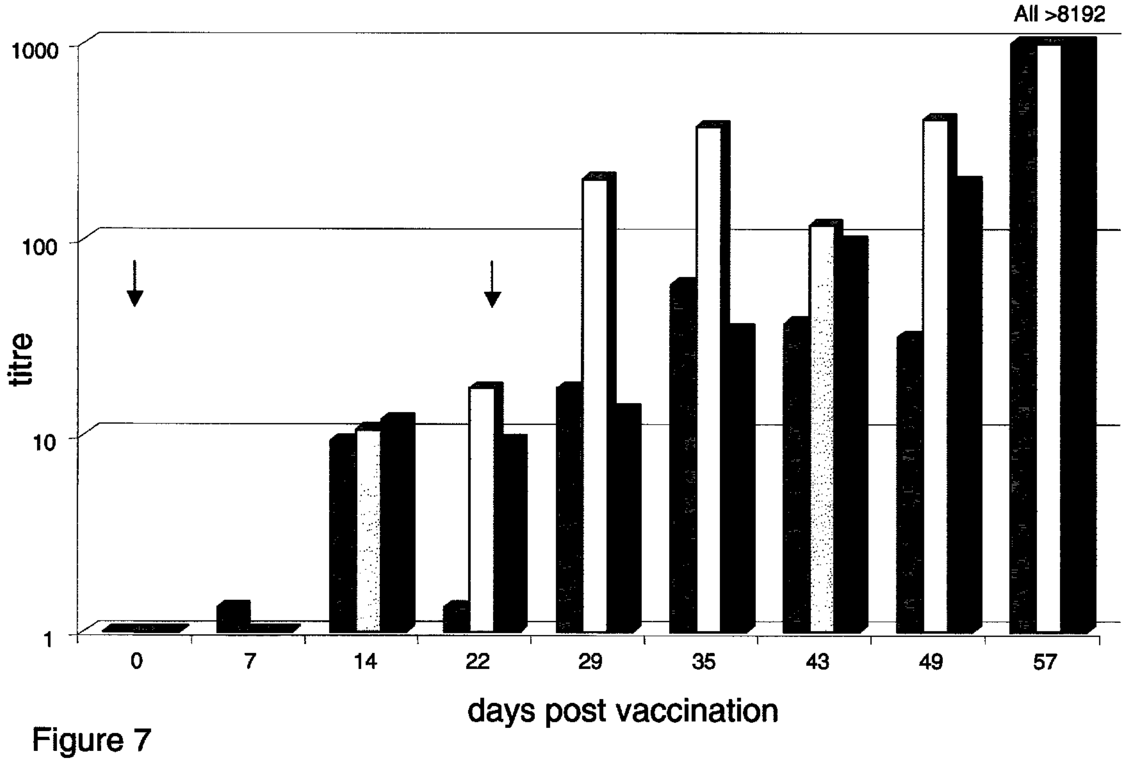
FIG. 7. NPLA titres post vaccination. Pigs were vaccinated on day 0 and given a booster dose on day 22. Pigs were challenged on day 49 with CSFV. Whole blood samples were collected on day 0 and then at weekly intervals with serum assayed for the presence of NPLA antibodies. Mean NPLA titres for vaccinated groups are shown. □=Unmodified rPAdV-gp55 s/c, □=Modified rPAdV-gp55 s/c, ■=Modified rPAdV-gp55 oral. ↓=vaccination.
Figure 8:
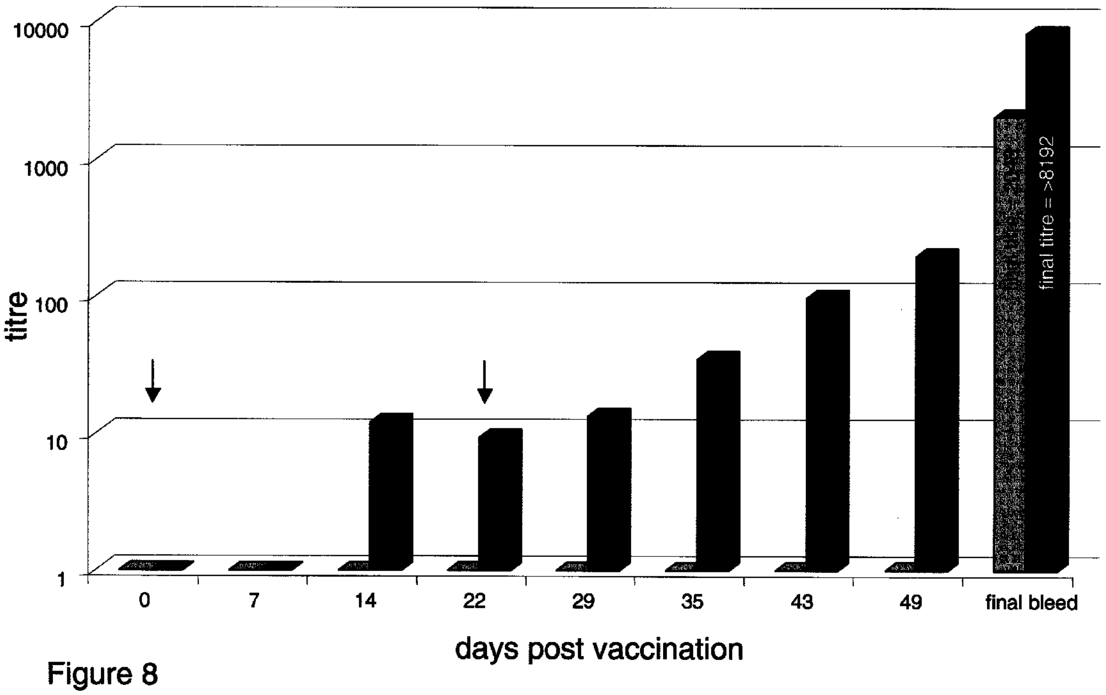
FIG. 8. Development of CSFV specific neutralising antibodies in orally vaccinated pigs. Pigs were vaccinated orally on day 0 and given a booster dose on day 22. Pigs were challenged on day 49 with CSFV. Whole blood samples were collected on day 0 and then at weekly intervals with serum assayed for the presence of NPLA antibodies. Mean NPLA titres for vaccinated groups are shown. □=Unmodified rPAdV-gp55*, ▨=Modified rPAdV-gp55. *=separate experimental data in Hammond et al., 2003. ↓=vaccination.
Figure 9:
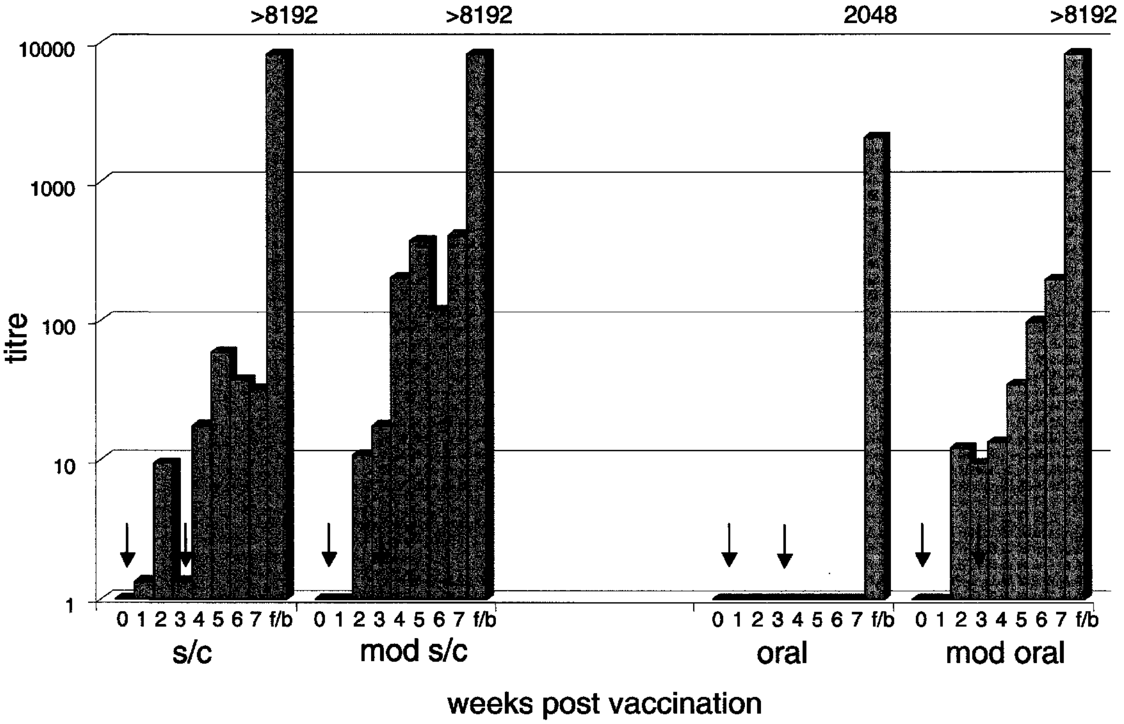
FIG. 9. Comparison of development of CSFV specific neutralising antibodies in vaccinated pigs. Pigs were vaccinated orally on day 0 and given a booster dose on day 22. Pigs were challenged on day 49 with CSFV. Whole blood samples were collected on day 0 and then at weekly intervals with serum assayed for the presence of NPLA antibodies. Mean NPLA titres for vaccinated groups are shown. ↓=vaccination. s/c=unmodified vaccine given sub-cutaneously, mod s/c=modified vaccine given sub-cutaneously, oral=unmodified vaccine given orally*, mod oral=modified vaccine given orally. *=separate experimental data in Hammond et al., 2003.
Figure 10:
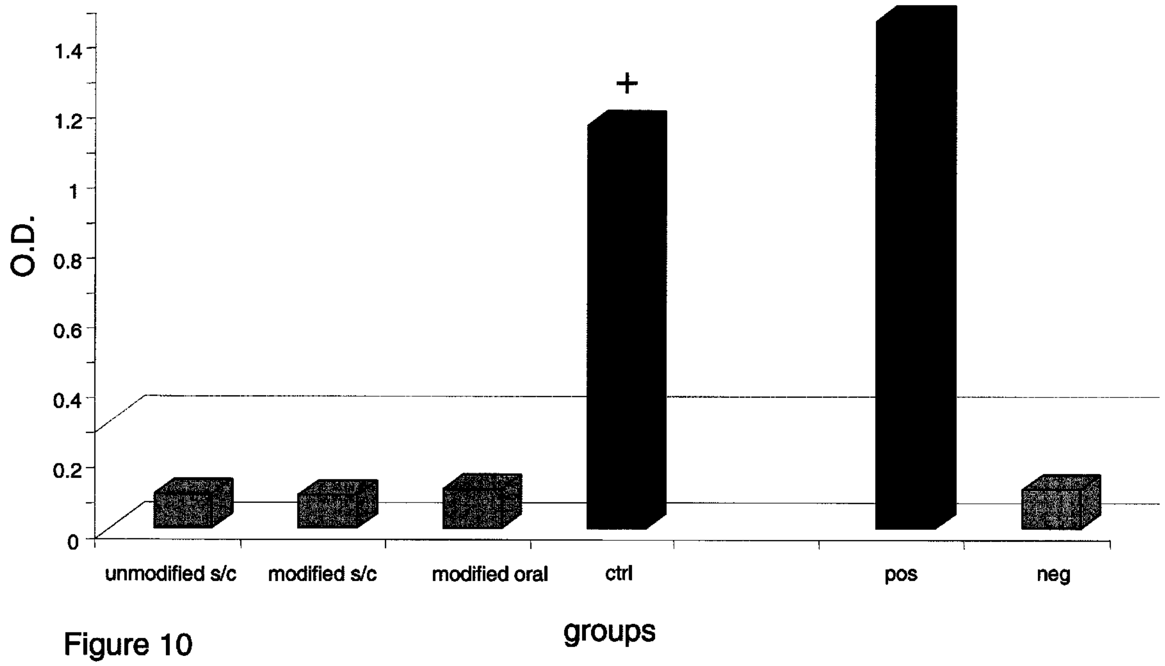
FIG. 10. CSFV antigen detection in the spleens of pigs. Following post mortem, spleen samples were analysed by antigen capture ELISA for the presence of CSFV antigen. Mean antigen titres for groups are shown. Pos=positive control spleen sample, neg=negative control spleen sample, +=euthanased.

Development of CSFV specific neutralising antibody: All pigs were bled on day 0 and then at weekly intervals until termination of the experiment and sera tested for the presence of neutralising antibodies against CSFV by NPLA (Terpstra et al., 1984). NPLA titres are shown in FIGS. 7-9.

Control pigs: Control pigs did not develop detectable CSFV neutralising antibody Group 1: All pigs developed detectable CSFV neutralising antibody by day 14 post vaccination, with one pig showing a detectable titre at day 7. The levels were boosted by administration of the second dose. All pigs survived challenge and had post challenge titres of >8192.

Group 2: All pigs developed detectable CSFV neutralising antibody by day 14 post vaccination and these levels were boosted by administration of the second dose. All pigs survived challenge and had post challenge titres of >8192.

Group 3: All pigs developed a detectable CSFV neutralising antibody by day 14 post vaccination and these levels were boosted by administration of the second dose. All pigs survived challenge and had post challenge titres of >8192.

Test for the presence of CSFV antigen in the spleen of pigs: The presence of CSFV antigen in the spleen of challenged pigs was determined by antigen capture ELISA [Shannon et al., 1993] and levels are shown in FIG. 9.

Control pigs: Control pigs had high levels of antigen in their spleens, indicative of ongoing infection at termination.

Group 1: None of the pigs were positive for CSFV antigen in the spleen demonstrating that all were disease and virus free at the end of the experiment.

Group 2: None of the pigs were positive for CSFV antigen in the spleen demonstrating that all were disease and virus free at the end of the experiment.

Group 3: None of the pigs were positive for CSFV antigen in the spleen demonstrating that all were disease and virus free at the end of the experiment.

From the above-described studies, it is demonstrated that a plasmid vector containing the PAdV-4 fibre gene was transfected into PK15 and ST cells and stably transfected cell lines expressing the PAdV-4 fibre were produced.

Recombinant PADV-3 (rPAdV-gp55) was shown to contain both PAdV-3 and PAdV-4 serotype fibres following passage through the PK15-743 cell line expressing the PAdV-4 fibre. This modified recombinant vaccine was administered to pigs and its efficacy evaluated in a CSFV challenge trial.

The modified vaccine completely protected pigs from lethal challenge with CSFV when given as sub-cutaneous injection or by the oral route. No significant differences in temperature responses post-challenge, or in the clearance of CSFV antigen from the spleen were detected between pigs given the modified and the unmodified vaccines. However, the modified vaccine given by the sub-cutaneous route generated the highest levels of NPLA antibodies out of all 3 groups, greater than those detected in the unmodified vaccine group. In addition, the inventors have previously demonstrated that when the unmodified vaccine is given by the oral route, no NPLA antibody titre can be detected before challenge, even following a booster dose [Hammond et al., 2001; Hammond et al., 2003]. In this experiment very significant levels of NPLA antibodies were detected in the oral group after only a single dose, and these levels were boosted by the administration of a second dose. This finding provides excellent evidence that the modified vaccine containing both the PADV-3 and PAdV-4 fibre proteins is being targeted to a wider variety of tissues in the pig than the unmodified vaccine, and as a consequence is generating a more extensive immune response in the host.

From the above data it can be concluded that modified rPAdV-gp55 is effective at generating serum neutralising antibodies against gp55 when administered orally, whereas unmodified vaccine is not. As such, this chimeric vaccine with both the PAdV-3 and PAdV-4 fibres has altered and/or increased the magnitude of the immune response in the pig. Such vaccines may be produced to allow for effective oral delivery. Given the exemplary embodiments taught herein, the techniques developed will allow the PAdV-4 fibre to be incorporated into any PAdV-3-based vaccine to improve efficacy by targeting delivery. In addition, other adenovirus vectors and cell lines may be produced in which the uses of a double fibre system will allow for an increased tropism of the recombinant adenoviral vaccine.

There are numerous references in the literature that provide further background to the present invention. Some of these references are provided below and are incorporated herein by reference in their entirety.

Amalfitano, A., and Chamberlain, J. S. (1997). Isolation and characterization of packaging cell lines that coexpress the adenovirus E1, DNA polymerase, and preterminal proteins: implications for gene therapy. Gene Ther 4, 258-263.

Amalfitano, A., Begy, C. R., and Chamberlain, J. S. (1996). Improved adenovirus packaging cell lines to support the growth of replication-defective gene-delivery vectors. Proc Natl Acad Sci 93, 3352-3356.

Bilbao G., Gomez-Navarro J., & Curiel D. T. (1998). Targeted adenoviral vectors for cancer gene therapy. In: Gene therapy of cancer, Ed Walden et al, Plenum Press, New York.

Chiu C. Y., Wu E., Brown S. L., Von Seggern D. J., Nemerow G. R., & Stewart P. L. (2001). Structural analysis of a fibre-pseudotyped adenovirus with ocular tropism suggests differential modes of cell receptor interactions. Journal of Virology 75, 5375-5380.

Chroboczek, J., Ruigrok, R. W. H., and Cusack, S. (1995). Adenovirus fibre. Curr Top Microbiol Immunol 199, 163-200.

Dmitriev, I., Krasnykh, V., Miller, C. R., Wang, M., Kashentseva, E., Mikheeva, G., Belousova, N., and Curiel, D. T. (1998). An adenovirus vector with genetically modified fibres demonstrates expanded tropism via utilization of a coxsackievirus and adenovirus receptor-independent cell entry mechanism. J Virol 72, 9706-13.

Dolph, P. J., Huang, J. T., and Schneider, R. J. (1990). Translation by the adenovirus tripartite leader: elements which determine independence from cap-binding protein complex. J Virol 64, 2669-2677.

Dolph, P. J., Racaniello, V., Villamarin, A., Palladino, F., and Schneider, R. J. (1988). The adenovirus tripartite leader may eliminate the requirement for cap-binding protein complex during translation initiation. J Virol 62, 2059-2066.

Douglas, J. T., Miller, C. R., Kim, M., Dmitriev, I., Mikheeva, G., Krashnykh, V., and Curiel, D. T. (1999). A system for the propagation of adenoviral vectors with genetically modified receptor specificities. Nat Biotechnol 17, 470-475.

Einfeld D. A., Brough D. E., Roelvink P. W., Kovesdi I., & Wickham T. J. (1999). Construction of a pseudoreceptor that mediates transduction by adenoviruses expressing a ligand in fibre or penton base. Journal of Virology 73, 9130-9136.

Gall, J., Kass-Eisler, A., Leinwand, L., and Falck-Pedersen, E. (1996). Adenovirus type 5 and 7 capsid chimera: fibre replacement alters receptor tropism without affecting primary immune neutralization epitopes. J Virol 70, 2116-2123.

Hammond J. M., Jansen E. S., Morrissy C. J., Hodgson A. L. M., & Johnson M. A. (2003). Protection Of Pigs Against 'In Contact' Challenge With Classical Swine Fever Following Oral Or Sub-Cutaneous Vaccination With A Recombinant Porcine Adenovirus. Virus Research 97, 151-157.

Hammond J. M., Jansen E. S., Morrissy C. J., Williamson M. M., Hodgson A. L. M., & Johnson M. A. (2001). Oral and sub-cutaneous vaccination of commercial pigs with a recombinant porcine adenovirus expressing the classical swine fever virus gp55 gene. Archives of Virology 146, 1-7.

Hammond J. M., McCoy R. J., Jansen E. S., Morrissy C. J., Hodgson A. L. M., & Johnson M. A. (2000). Vaccination with a single dose of a recombinant porcine adenovirus expressing the classical swine fever virus gp55 (E2) gene protects pigs against classical swine fever. Vaccine 18, 1040-1050.

Hirt, B. (1967). Selective extraction of polyoma DNA from infected mouse cell cultures. J Mol Biol 14, 365-369.

Kleiboeker, S. B. (1995), Sequence analysis of the fibre genomic region of a porcine adenovirus predicts a novel fibre protein. Virus Res 39, 299-309.

Krashnykh, V. N., Mikheeva, G. V., Douglas, J. T., and Curiel, D. T. (1996). Generation of recombinant adenovirus vectors with modified fibres for altering viral tropism. J Virol 70, 6839-6846.

Magnusson M. K., Hong S. S., Boulanger P., & Lindholm L. (2001). Genetic retargeting of adenovirus: novel strategy employing "deknobbing" of the fibre. Journal of Virology 75, 7280-7289.

Melkonyan, H., Sorg, C., and Klempt, M. (1996). Electroporation efficiency in mammalian cells is increased by dimethyl sulfoxide (DMSO). Nucleic Acids Res 24, 4356-4357.

Reddy, P. S., Idamakanti, N., Song, J.-Y., Lee, J.-B., Hyun, B.-H., Park, J.-H., Cha, S.-H., Bae, Y.-T., Tikoo, S. K., and Babiuk, L. A. (1998). Nucleotide sequence and transcription map of porcine adenovirus type-3. Virology 251, 414-426.

Reddy, P. S., Nagy, E., and Derbyshire, J. B. (1995). Sequence analysis of putative pVIII, E3 and fibre regions of porcine adenovirus type 3. Virus Res 36, 97-106.

Shannon A D, Morrissy C, Mackintosh S G and Westbury H A. (1993). Detection of hog cholera virus antigens in experimentally-infected pigs using an antigen-capture ELISA. Vet. Microbiol. 34: 233-248.

Shayakhmetov D. M., Papayannopoulou T., Stamatoyannopoulos G., & Lieber A. (2000). Efficient gene transfer into human CD34+ cells by a retargeted adenovirus vector. Journal of Virology 74, 2567-2583.

Sheay, W., Nelson, S., Martinez, I., Chu, T. H., Bhatia, S., and Dornburg, R. (1993). Downstream insertion of the adenovirus tripartite leader sequence enhances expression in universal eukaryotic vectors. Biotechniques 15, 856-862.

Shinagawa, M., Matsuda, A., Ishiyama, T., Goto, H., and Sato, G. (1983). A rapid and simple method for preparation of adenovirus DNA from infected cells. Microbiol Immunol 27, 817-822.

Shiraishi M., Nagahama M., Obuchi Y., Taira K., Tomori H., Sugawa H., Kusano T., & Muto Y. (1998). Successful gene transfer to the porcine liver in Vivo with an adenoviral vector. Journal of Surgical Research 76, 105-110.

Stevenson, S. C., Rollence, M., Marshall-Neff, J., and McClelland, A. (1997). Selective targeting of human cells by a chimeric adenovirus vector containing a modified fibre protein. J Virol 71, 4782-90.

Terpstra, C, Bloemraad, M and Gielkens, A J L. (1984). The neutralising peroxidase-linked assay for detection of antibody against swine fever virus. Vet. Microbiol. 9: 113-120.

von Seggern, D. J., Chiu, C. Y., Fleck, S. K., Stewart, P. L. and Nemerow, G. R. (1999). A helper-independent adenovirus vector with E1, E3 and fibre deleted: structure and infectivity of fibreless particles. J Virol 73, 1601-1608.

von Seggern, D. J., Kehler, J., Endo, R. I., and Nemerow, G. R. (1998). Complementation of a fibre mutant adenovirus by packaging cell lines stably expressing the adenovirus type 5 fibre protein. J Gen Virol 79, 1461-1468.

Von Seggern D. J., Huang S., Fleck S. K., Stevenson S. C., & Nemerow G. R. (2000). Adenovirus vector pseudotyping in fibre-expressing cell lines: improved transduction of Epstein-Barr virus-transformed B cells. Journal of Virology 74, 354-62.

Wang, Q., Jia, X. C., and Finer, M. H. (1995). A packaging cell line for propagation of recombinant adenovirus vectors containing two lethal gene-region deletions. Gene Ther 2, 775-783.

Watkins, S. J., Mesyanzhinov, V. V., Kurochkina, L. P., and Hawkins, R. E. (1997). The 'adenobody' approach to viral targeting: specific and enhanced adenoviral gene delivery. Gene Ther 4, 1004-1012.

Wickham, T. J., Tzeng, E., Shears II, L. L., Roelvink, P. W., Li, Y., Lee, G. M., Brough, D. E., Lizonova, A., and Kovesdi, I. (1997). Increased in vitro and in vivo gene transfer by adenovirus vectors containing chimeric fibre proteins. J Virol 71, 8221-8229.

Wirtz, S., Galle, P. R., and Neurath, M. F. (1999). Efficient gene delivery to the inflamed colon by local administration of recombinant adenoviruses with normal or modified fibre structure. Gut 44, 800-807.

Zhang, Y., Feigenblum, D., and Schneider, R. J. (1994). A late adenovirus factor induces eIF-4E dephosphorylation and inhibition of cell protein synthesis. J Virol 68, 7040-7050.

Sequence Information

SEQ ID NO:1: PAdV4 Fibre gene from 2250 bases of sequence from Fibre towards right hand end (rhe). There is a good match with PAdV3 fibre (bold) but all subsequent sequence is novel.

AACCCACCTGGAACACCAAGTGCCAGATGCTCCAGTTTTTTCTACCGCGG

GAGTTTCGAAAGTTTACCCTCAGATACTGTAGTCAGACACAAAGATGTAA

CTGCCWGCATGAGAAAGTTTATTGGCAATAAAGCTACTGGAAACGATGCG

TGTGGTGATCTTTCCCCCTCCCCCAAATTTCATTTTGTAACATACCCTAT

GGGAAGGCCCCGGCCCACAGTCAGCCACAGTCTCAAGTTGCTCCAGCTCA

GGTGAGGTAATGCTGATGAACCCAGGCGATATCAGTCTCGCATCCAAGGT

GTGATCCAAACTCTGTGAAAATCATACTCCGCTTGTAAACTTTCGCCAAG

GCACCGGGGTTCCATACACCATCAATCTTCGCAGACGTCGCCGCCGTGCG

CCGTCCCGAAAAGCCGGGTAGAACACTCTCGGTCGAGGTCCCCCAACTCT

CAGCAACCTAAAAGCCTCCTGAAGCAACTCCCTGCTCTGAACCGCACACT

GCCTCACATCACGTTCATGCAGAGACATACATCCAGTACACAAGCGTATA

AAGTAGTAATTAGTTGCAGTACAGAGAAATTTCACAGACGGGCCTGACAG

TTGCTGCTTCAAAAGCCAAAAGTCATTCCCCTGTCTGCAGCAAAACACCA

CAAAGTGCAGCCCCGCCACCATATAGGAGCCCCTGCAAGAGATAGCTTTA

GGTAAGTCAACACACACCCTCTTCTGCATACCAGATGAAGCTGCGGTTAA

AGAAACAGCCCCTGGGATCACAGACGTAGCCAAAGGTCTTCACCACCACA

CTCCTAGCCCTACATTGCAAGAGAGTGRGGGCTGTCaCAGKTGRMCAATG

TATAGAAAGCACCTCTCGACCATACAAGTAATTtCCCCSAAWaCAGATtG tTTAACTCCAAGGSCCCGGGGgcCAGACCCATCCCAGTtCTACGGAGACA

TTGCAAAGTGGAGCCAGAAGCAACCAAATCCCAAGGCACCGGAAGATCTA

AGTAAGCTGTGAAACATGCTGCAGGTGGAGTGGTGCTTACCGCTCCAACT

AGATGCTTAGAGTCACATGGTTCAACAGAAGTCATTGTCCTGGAAGAGGA

AGAGGGAAAGCATTAAAGCACCGAAACAGCTCAATGGGGGGGCTGGTGTG

GTACACAGCCACCATACGGGAACCAAGAAAAGTCAACAGGCCAGAGGCCA

AATCCTGCTGGGACTCCGGAGTTGCAAACAGCCGAGAGCCCGCCGTGACT

GTGATAGTGTGCCTGCCTTGAGGTAAATCAAGCATGCAGCAACAATGCAG

AAAAGACTCAGAGCGAGTACCAGGGCGAGTTTCCAAATCAAAGCGAATCA

GCAAGTAATCATAAACCAAGGATCTGATCACATCCAgCCAAAGSWCKWCM

CGAAGGCAAAGTAGGATCCCCTGGCACATCCGTGATGTACAGGTGCCAGG

ACCAAGCGCTGTACACGAAAGTGCCGGACGCCATCTTGCGTACAGATCAC

TGACCCGTGGAGCCGAAACCGCCGGCACCCCTGTCGGTAGGCTGCAGGTC

-continued

GTCCACCAGCTGGCACACGGGTCTCTCAAATTTCAGGAAAACCAGCTGCG

CGATCCGGTCCCCGGGAGCGATAAACACAGGCAGAGGCCCACTGTTCGCC

AACAGCACTTTCACTCGCCTGTAAGTCCGGGTCAATTGTTCCCGCACAGA

CGTACACGCCGCGCAACGACAACTCGATCGTGAAAAAATCTGCCCGTAGG

GCCCAGGCGGAGGACTTATGGCGATCCCAGAACGGATGATAGTTCGGTCC

CCCGGTTCCATGATACGAGCCTCCGGCGAGCAAAACGTCTATCCCCCGTG

AAGCCGCCGTACCGAAAACAGCCGGCCCCCCCCGTCCCGCTAACTTCCCC

TTTAAGATCCGGAGTGGTCCTGACGGCTCAGAGGGAAAAACCGCGAAAAA

ATTCCGCGAACTCCGCAAAAACCCGAACGGAGTACCGCCCCCGGGAATCC

GTGAACTGACATTGGCCGACTTTTATGGCGCCCGGCATGTCGATAGTGAC

AATACGGGAAGGGAACCAATTCACGCATTCTGGGCAGTGTGGGAGAAAGC

GGACTTACACAATGTGTCTTCGCACCACGGGAAAAGATTACTCGATACCT

CATAAGGTGATG

SEQ ID NO:2 1858 bases of sequence from Fibre from PadV1 towards right hand end (rhe) There is a good match with PAdV3 in some sections (in bold) novel sequence in normal font

TATAAACCAGTTCCACCATGGGACCGAAGAAGCAGAAGCGCGAGCTCCCC

GAGGACTTCGATCCAGTCTACCCCTATGACGCCCCGCAGCTGCAGATCAA

TCCACCCTTCGTCAGCGGGGACGGATTCCACCAATCCGTGGACGGGGTGC

TGTCCCTGCACATCGCACCGCCCCTCGTCTTTGACAACACCAGGGCCCTC

ACCCTGGCCTTCGGGGATGGTCTACAGCTCTTTAACAACAAGCTCATCGT

TGCCACTGAGGGATCTGGGCTGGTCATCACCACGGATGGCAAGCTGGTCC

TCCAGGTCACCTCCCCCCTCACCCTAGCACCCGATGGCATCTcCCcTGTC

CCTGGGcCCCcGGTCTCTCTAGCTCAaGATGACAaGACTCAGCCsTGCAA

GGTCACATCTCCCCTGCAGCTCCaAAAGCAACTCCCTCGCCCTTTCCCTC

GGCAGCGGTCTCCAAAACACCGAGGGTGGCcGTAGCtTGTCAAGCTGGGG

GCTGGTCTCACCACGGACAACAGTCAGTCAGTGACAGTCAAGGTGGGAGA

CGGTCTTAAGCTGAACGAAGGAGGGCTGCTCACCGTCCCCGTAACAGCAC

CACTTGTGTCCGGCGCACCCGGACTATCACTTTAACTACTCCTCCACTGA

TTTCGAACTTGATAACGGCAGCCTCCGTCTGCGTCCTAAGCCGATCTCCG

TCACGGCGCCACTGCAATCTACCGCTGACACCATCTCCCTGAAGTATTCT

GACACTGACTTCTCTTTGGAGGATAACACCACCCTCACTTTAACACCTAA

ATTAAAACCGTACACACTGTGGACCGGTAATTCAGATACAGCTAATGTGA

TCCTCAATCACAGCTCCACCCCCAATGGTACATTATTTCTATGTCTGACA

CGTGTGGGTGGRTAGTTTTAGCACTTTGCCCTGAAGACATCATCCCTACA

TTTAGTGATATGACAAACAGCTATCTTATTTTTGATACTTTGTCGACTCA

GACTCTCACTTATAGGAGTTTGATTAGATCAACACGACGTCATTAGCCCA

CAGtCCACAGGACTCAGTCCAGCCTGGTTAATGCCAAGCACCTTTATTTA

CCCTAACTCATCGGGCTCAACTTTGACATCATTCGTAAGAATTAAAGCAA

-continued

CAAATGTTCATGTGGATATCAGAGTCAACAGCCTCTCCACTAACGGTTTT

AGTCTTCAGTTTGAATTTGAAAACATGATCATCTCCAGTGCCTTCTCCAC

CTCCTACGGGACCTTCTGCTACGTGCCCCAGAGTGCCTAGAGAACCCTGG

CCGTCAGCCGGCCTCCCCCTTCCCATACCACCCGGTAGACCACCCGCTCC

ATGTTTCTGTATGTGTTCTCCTCCCGCCGCTTGTGCAGCACCACCTCCCG

CTGCTCGAGCTGAGGATCCGTGATGGACACAAAGCCAGGAAGACACATCC

TCAGCTCCGTGGGGGCGTCCAACAACTGTTTGTGCAAGGAAAATATGAAA

CAATAAAGACTCAGAGAAAAACAAGTTCATATGATTTTTTCTTTTATTGA

TTGGGGGATTTGATTCAGGTGGGGTGTACATATCACAAAAAAATCACATC

AGCAGCTACACCCTGGAAACATTCAGACAGGGGTAAGGACAGCGCCCTCA

GCTTCTGGAACAAACATTAGAAATATTTAACTCGTCTTGGAGCTAACACT

CTTTTTCCCAGAACACATAAACATCCTGTAGA

SEQ ID NO:3 969 bases of sequence from PAdV2 Fibre towards right hand end (rhe). There is a good match with PAdV3 in some sections (in bold) which includes the complete rhe of PAdV3. Novel sequence in normal font AGTGGGGTTCAAAAAAGTTACATAAnCGCGCTTCTCGTGCAGAGAGAGCC GGGnAnnGCGCCTCTTCAGCAGTGGGTCGTGGGCCGTGAGAGGGGGCTGA

TGGGAAGATGGCCGGTGACTCCTCTCGCCCCGCTTTCGGCTTCTCCTCGT

CTCGCTCTCCTTGTCTCTCTCTGTGTCAGCGCAGAAACTAGTGTGAGCGA

ACAACGCGAGGGGGCCGGTGATATACCCnCAGCTGATGTGGCCACAGCTG

CTATCGGnTAATCACTACCCCATCGTACGATCGnAATTCCCCCGCCTCCT

CGTTnCGATTAACCCACCCAGAAGTCTCGGGAATTCCCGCCAGCCGGGCT

CCGACCCGCGACGTGCGGACTTTGACCCCGCnCCTCGGACATTGACCGGT

CCCACGCCACGTCACTTTCCCACTCGACGTCCCGTTCCCGCGCTnCGTCA

CACCCCTCTCCATGAATCTGCTGCAACCGCCTCGAACCCTCTCTTCCAAT

CAACTCGCCATTAAAGGGGCAATAAAAGTGTAGGGTATATGGATTGATGA

TGGCCCAGGTGACCAGGTCCGAGCGCTTGATCGATTCCGTGGGAAGTGGA

TGTCAGCTAAGCTCCTAATGACAACCGCCAACCACGGCTGCAGAAGCTCT

TCCCTCTAGAGACGCGAGCTAGCATAGACATACTCCATCTATACACTCGC

CGTAGACAATGTCATACGCAAATGGGAGGACTAAGGACATCCCGGATCCA

CCACCTGGGATGTACTCCATCCATCGGGACACTTAAACAGCAATAAGAAA

GACGCAATTGTTGACGCAGAAATTTGGCTAGAGAGGCGGGCAGGACTCAT

GAGCCTAGAGACCACCCAATTGGGAAAGTGACCTCCCCTCCCCCCGTGGA

AAACGTGGTATCAAACGAGATCGACAATGCAATTCGGTCACTTTAGGGGT

ACGAGGATATATCACGGA

SEQ ID NO:4: PAdV2 fibre from second set of data. 1176 bases of sequence give good match with PAdV3 but in reverse orientation to left hand end (bold) suggesting last primer worked off both ends of genome probably from ITR and gave dual sequence information

AAAAAAGGCAGGAGCGATGATTGATAGCTCGAGGAATAGCTCAGTCACCA

CATCCCTTCCCTGCACCACTTATAAGGGTATATATAGGCAGAGACACAGA

CAATCAGTCATCATCACATGCTGTTTATTGAGGTTAATGATTAATCGCGG

GGGCGCTTCATAGACAGGTCCAAAGGTTGTTCGCTGCATGAGTCATAGCA

GTACTTCCTCTTGCGTCCTGGCAGGTCTCCAAGTCCCGGGGAACCCGACC

TGTGAGGTGCTGGAGAAACAGCTTCTAAAAAGACAAAAAATGGGAAATAG

CACATGAGATTTCTTACAAGCACTTTTTCCTTTTTTTCCACATAATCCCA

CAAATGTCCAAAAACACTCACCATAGACAGCAAAGGCATGCATCCTCATG

TAGCACAGACTGCACTTCAGATTGGGGTCCTTGGAGTGAAAGCGATGGTA

ATCACAAGAGCGGCAGTTCACACCAGGTACCTCGGGGCAGTCCAACACAA

ACGGAGAGGGTGGCGCAAGTGGGTCCTCAAACACCACATCAGCCAGTTCA

GACAGCACCTCCGCAGCCACCGCGCTGATATCCTCCTCATTACTGTCCCC

CTCTTCTGGGGGGTCCATCTCAAAGACCCCCTGAGAGCCACCTGAGTCAC

CAGCGGCACTCCCACCACTGTCCTCAGCTACACCCCCCTCAGTCACAATC

ACCTCCACCTCGTCCACACTGTCCAGCCACTCGTCCGGCAGTCCATCGAC

CAGACTCTCCCAGCACGGCTCACAGAAGCCCTCATCCCCCGGAGAGGGGT

CGCGCAGATCCACCGGGTCCCATTCCAGCACCGGCACCACCTCGGGGTTT

CCGTCCCAGTCCAGGTGAAGTCTGTTCGCCATGTCGAGGGTCTGTTCCGC

TGAGAGAAAACTCTACTCCCTTCGGACTCAAGAGTAGTGACTCTCGGGCG

CTGCGCGGACTATATACACTGAGGAGAAAAAATACACCCACACACGTCAT

CTCGGGCGGGCGCCGCGACCTCTCAGCGCGAAGGAAACCCCGGCTCAGGT

GAATGGTGTCCCGTCGTCAGTGGGGATACGAGCGGCGACGGTGTGTGGAA

ATGCCACACCGGAGGGCGAGGGTCAGTCCAAAAGCAAAAATTCCCGCTAA

CTTCCACTTGTTGGAAATATCTCTGC

SEQ ID NO:5 Reverse complement of PAdV2 contig

GCAGAGATATTTCCAACAAGTGGAAGTTAGCGGGAATTTTTGCTTTTGGA

CTGACCCTCGCCCTCCGGTGTGGCATTTCCACACACCGTCGCCGCTCGTA

TCCCCACTGACGACGGGACACCATTCACCTGAGCCGGGGTTTCCTTCGCG

CTGAGAGGTCGCGGCGCCCGCCCGAGATGACGTGTGTGGGTGTATTTTTT

CTCCTCAGTGTATATAGTCCGCGCAGCGCCCGAGAGTCACTACTCTTGAG

TCCGAAGGGAGTAGAGTTTTCTCTCAGCGGAACAGACCCTCGACATGGCG

AACAGACTTCACCTGGACTGGGACGGAAACCCCGAGGTGGTGCCGGTGCT

GGAATGGGACCCGGTGGATCTGCGCGACCCCTCTCCGGGGGATGAGGGCT

TCTGTGAGCCGTGCTGGGAGAGTCTGGTCGATGGACTGCCGGACGAGTGG

CTGGACAGTGTGGACGAGGTGGAGGTGATTGTGACTGAGGGGGGTGTAGC

TGAGGACAGTGGTGGGAGTGCCGCTGGTGACTCAGGTGGCTCTCAGGGGG

TCTTTGAGATGGACCCCCCAGAAGAGGGGGACAGTAATGAGGAGGATATC

AGCGCGGTGGCTGCGGAGGTGCTGTCTGAACTGGCTGATGTGGTGTTTGA

GGACCCACTTGCGCCACCCTCTCCGTTTGTGTTGGACTGCCCCGAGGTAC

CTGGTGTGAACTGCCGCTCTTGTGATTACCATCGCTTTCACTCCAAGGAC

-continued

CCCAATCTGAAGTGCAGTCTGTGCTACATGAGGATGCATGCCTTTGCTGT

CTATGGTGAGTGTTTTTGGACATTTGTGGGATTATGTGGAAAAAAAGGAA

AAAGTGCTTGTAAGAAATCTCATGTGCTATTTCCCATTTTTTGTCTTTTT

AGAAGCTGTTTCTCCAGCACCTCACAGGTCGGGTTCCCCGGGACTTGGAG

-continued

ACCTGCCAGGACGCAAGAGGAAGTACTGCTATGACTCATGCAGCGAACAA

CCTTTGGACCTGTCTATGAAGCGCCCCCGCGATTAATCATTAACCTCAAT

AAACAGCATGTGATGATGACTGATTGTCTGTGTCTCTGCCTATATATACC

CTTATAAGTGGTGCAGGGAAGGGATGTGGTGACTGAGCTATTCCTCGAGC

TATCAATCATCGCTCCTGCCTTTTTT

---

The invention claimed is:

1. A recombinant adenoviral vector comprising an adenovirus that comprises a fibre gene native to said adenovirus and further comprises a second fibre gene that is heterologous to said adenovirus, wherein said second fibre gene is acquired by said recombinant adenovirus by growth of said recombinant adenovirus in a cell line that stably expresses said second fibre gene, wherein the adenovirus is a recombinant porcine adenovirus selected from the group consisting of recombinant PAdV-1, recombinant PAdV-2, recombinant PAdV-3, recombinant PAdV-4, recombinant PAdV-5, recombinant PAdV-6, and recombinant PAdV-7.

2. A recombinant adenoviral vector comprising an adenovirus that comprises a fibre gene native to said adenovirus and further comprises a second fibre gene that is heterologous to said adenovirus, wherein said second fibre gene is acquired by said recombinant adenovirus by growth of said recombinant adenovirus in a cell line that stably expresses said second fibre gene wherein said second fibre protein is the fibre protein selected from PAdV-1, PAdV-2, PAdV-3, PAdV-4, and PAdV-5.

3. The recombinant adenoviral vector of claim 1 or claim 2, wherein said recombinant adenoviral vector further comprises a third fibre protein that is different from said first or said second fibre protein.

4. The recombinant adenoviral vector of claim 1 or claim 2, wherein said recombinant adenoviral vector is replication competent.

5. The recombinant adenoviral vector of claim 1 or claim 2, wherein said recombinant adenoviral vector is replication-defective, wherein said recombinant adenoviral vector comprises a heterologous nucleotide sequence inserted into an essential region of the adenoviral genome and said cell line that stably expresses said fibre gene also expresses the essential region of the adenoviral genome into which the heterologous nucleotide sequence has been inserted.

6. The recombinant adenoviral vector of claim 1 or claim 2, wherein said recombinant adenovirus comprises a heterologous nucleotide sequence inserted into a nonessential region of the adenoviral genome wherein said heterologous nucleotide sequence is a gene that encodes a protein selected from the group consisting of an immunomodulator, an antigen, a pathogen, an immunogenic polypeptide, a therapeutic polypeptide, a growth hormone, and a cytokine.

7. A composition capable of inducing an immune response in a mammalian subject, said composition comprising a recombinant adenoviral vector of claim 1 or claim 2 and a pharmaceutically acceptable excipient.

8. A method for eliciting an immune response in a mammalian subject comprising administering a composition of claim 7 to the mammalian subject.

9. A method of preparing an adenovirus vector of claim 1 or claim 2 comprising: a, culturing a recombinant host cell that expresses an adenoviral fibre gene under conditions suitable for infection of said cell with adenovirus, b, contacting said cell with a recombinant adenovirus vector which comprises the adenovirus sequence(s) essential for encapsidation and a heterologous gene that encodes a heterologous protein and wherein said recombinant adenovirus comprises a fibre gene that is different from the fibre gene in said host cell; and optionally harvesting said adenovirus.

10. The method of claim 9 wherein the harvested adenovirus vector comprises a broader tissue specificity as compared to the adenovirus vector that is not contacted with said recombinant host cell.

11. The method of claim 9 wherein said adenovirus vector is optionally deleted in part or all of one or more adenoviral proteins that are non-essential for replication.

12. A vaccine for protecting a mammalian host against infection comprising the recombinant adenovirus vector of claim 1 or claim 2 and optionally a pharmaceutically acceptable excipient.

13. A method of vaccinating an animal comprising administering to said animal a therapeutically effective amount of a vaccine of claim 12.

* * * * *